US007485617B1

(12) United States Patent
Pohl et al.

(10) Patent No.: US 7,485,617 B1
(45) Date of Patent: Feb. 3, 2009

(54) OSTEOINDUCTIVE MATERIALS

(75) Inventors: Jens Pohl, Hambrucken (DE); Rolf Bechtold, Heidelberg (DE); Michael Kruse, Mainz (DE)

(73) Assignee: Biopharm Gesellschaft zur Biotechnologischen Entwicklung von Pharmaka mbH, Heidelberg (DE)

( * ) Notice: Subject to any disclaimer, the term of this patent is extended or adjusted under 35 U.S.C. 154(b) by 37 days.

(21) Appl. No.: 10/550,958

(22) PCT Filed: Mar. 26, 2004

(86) PCT No.: PCT/EP2004/003238

§ 371 (c)(1), (2), (4) Date: Sep. 28, 2005

(87) PCT Pub. No.: WO2004/084965

PCT Pub. Date: Oct. 7, 2004

(30) Foreign Application Priority Data

Mar. 28, 2003 (EP) ................................ 03007141

(51) Int. Cl.

| | |
|---|---|
| ***A61K 38/00*** | (2006.01) |
| ***A61K 38/16*** | (2006.01) |
| ***A61K 38/17*** | (2006.01) |
| ***A61K 38/18*** | (2006.01) |
| ***A61K 9/00*** | (2006.01) |
| ***A61B 17/56*** | (2006.01) |

(52) U.S. Cl. ......................... 514/2; 514/12; 514/772.1; 514/772.3; 424/407; 424/422; 424/423; 424/484; 424/486; 424/488

(58) Field of Classification Search ...................... None
See application file for complete search history.

(56) References Cited

U.S. PATENT DOCUMENTS 6,118,043 A 9/2000 Dingeldein et al.

FOREIGN PATENT DOCUMENTS

| | | | |
|---|---|---|---|
| EP | 0567391 | A1 * | 10/1993 |
| EP | 1074620 | A1 * | 2/2001 |
| WO | WO 94/15653 | A | 7/1994 |

* cited by examiner

*Primary Examiner*—Elizabeth C Kemmerer
(74) *Attorney, Agent, or Firm*—Rothwell, Figg, Ernst & Manbeck, P.C.

(57) ABSTRACT

The present invention concerns improved osteoinductive materials comprising matrix materials and morphogenetic roteins, wherein depending on the subject matter the proteins may be dimeric or monomeric proteins. The osteoinductive materials according to the present invention have improved properties. The invention further concerns methods for producing the respective improved osteoinductive materials.

25 Claims, 14 Drawing Sheets

SEQUENCE LISTING

```
<160> NUMBER OF SEQ ID NOS: 5

<210> SEQ ID NO 1
<211> LENGTH: 2703
<212> TYPE: DNA
<213> ORGANISM: Homo sapiens
<220> FEATURE:
<221> NAME/KEY: CDS
<222> LOCATION: (640)..(2142)
<220> FEATURE:
<221> NAME/KEY: misc_feature
<222> LOCATION: (2032)..(2034)
<223> OTHER INFORMATION: n is a, c, g, or t

<400> SEQUENCE: 1

ccatggcctc gaaagggcag cggtgatttt tttcacataa atatatcgca cttaaatgag      60

tttagacagc atgacatcag agagtaatta aattggtttg ggttggaatt ccgtttccaa     120

ttcctgagtt caggtttgta aaagattttt ctgagcacct gcaggcctgt gagtgtgtgt     180

gtgtgtgtgt gtgtgtgtgt gtgtgtgtga agtattttca ctggaaagga ttcaaaacta     240

gggggaaaa aaaaactgga gcacacaggc agcattacgc cattcttcct tcttggaaaa      300

tccctcagcc ttatacaagc ctccttcaag ccctcagtca gttgtgcagg agaaaggggg     360

cggttggctt tctcctttca agaacgagtt attttcagct gctgactgga gacggtgcac     420

gtctggatac gagagcattt ccactatggg actggataca aacacacacc cggcagactt     480

caagagtctc agactgagga gaaagccttt ccttctgctg ctactgctgc tgccgctgct     540

tttgaaagtc cactcctttc atggtttttc ctgccaaacc agaggcacct ttgctgctgc     600

cgctgttctc tttggtgtca ttcagcggct ggccagaggg atg aga ctc ccc aaa       654
                                          Met Arg Leu Pro Lys
                                          1               5

ctc ctc act ttc ttg ctt tgg tac ctg gct tgg ctg gac ctg gaa ttc       702
Leu Leu Thr Phe Leu Leu Trp Tyr Leu Ala Trp Leu Asp Leu Glu Phe
                10                  15                  20

atc tgc act gtg ttg ggt gcc cct gac ttg ggc cag aga ccc cag ggg       750
Ile Cys Thr Val Leu Gly Ala Pro Asp Leu Gly Gln Arg Pro Gln Gly
            25                  30                  35

acc agg cca gga ttg gcc aaa gca gag gcc aag gag agg ccc ccc ctg       798
Thr Arg Pro Gly Leu Ala Lys Ala Glu Ala Lys Glu Arg Pro Pro Leu
        40                  45                  50

gcc cgg aac gtc ttc agg cca ggg ggt cac agc tat ggt ggg ggg gcc       846
Ala Arg Asn Val Phe Arg Pro Gly Gly His Ser Tyr Gly Gly Gly Ala
    55                  60                  65

acc aat gcc aat gcc agg gca aag gga ggc acc ggg cag aca gga ggc       894
Thr Asn Ala Asn Ala Arg Ala Lys Gly Gly Thr Gly Gln Thr Gly Gly
70                  75                  80                  85

ctg aca cag ccc aag aag gat gaa ccc aaa aag ctg ccc ccc aga ccg       942
Leu Thr Gln Pro Lys Lys Asp Glu Pro Lys Lys Leu Pro Pro Arg Pro
                90                  95                  100
```

-continued

```
ggc ggc cct gaa ccc aag cca gga cac cct ccc caa aca agg cag gct      990
Gly Gly Pro Glu Pro Lys Pro Gly His Pro Pro Gln Thr Arg Gln Ala
            105                 110                 115

aca gcc cgg act gtg acc cca aaa gga cag ctt ccc gga ggc aag gca     1038
Thr Ala Arg Thr Val Thr Pro Lys Gly Gln Leu Pro Gly Gly Lys Ala
        120                 125                 130

ccc cca aaa gca gga tct gtc ccc agc tcc ttc ctg ctg aag aag gcc     1086
Pro Pro Lys Ala Gly Ser Val Pro Ser Ser Phe Leu Leu Lys Lys Ala
    135                 140                 145

agg gag ccc ggg ccc cca cga gag ccc aag gag ccg ttt cgc cca ccc     1134
Arg Glu Pro Gly Pro Pro Arg Glu Pro Lys Glu Pro Phe Arg Pro Pro
150                 155                 160                 165

ccc atc aca ccc cac gag tac atg ctc tcg ctg tac agg acg ctg tcc     1182
Pro Ile Thr Pro His Glu Tyr Met Leu Ser Leu Tyr Arg Thr Leu Ser
                170                 175                 180

gat gct gac aga aag gga ggc aac agc agc gtg aag ttg gag gct ggc     1230
Asp Ala Asp Arg Lys Gly Gly Asn Ser Ser Val Lys Leu Glu Ala Gly
            185                 190                 195

ctg gcc aac acc atc acc agc ttt att gac aaa ggg caa gat gac cga     1278
Leu Ala Asn Thr Ile Thr Ser Phe Ile Asp Lys Gly Gln Asp Asp Arg
        200                 205                 210

ggt ccc gtg gtc agg aag cag agg tac gtg ttt gac att agt gcc ctg     1326
Gly Pro Val Val Arg Lys Gln Arg Tyr Val Phe Asp Ile Ser Ala Leu
    215                 220                 225

gag aag gat ggg ctg ctg ggg gcc gag ctg cgg atc ttg cgg aag aag     1374
Glu Lys Asp Gly Leu Leu Gly Ala Glu Leu Arg Ile Leu Arg Lys Lys
230                 235                 240                 245

ccc tcg gac acg gcc aag cca gcg gcc ccc gga ggc ggg cgg gct gcc     1422
Pro Ser Asp Thr Ala Lys Pro Ala Ala Pro Gly Gly Gly Arg Ala Ala
                250                 255                 260

cag ctg aag ctg tcc agc tgc ccc agc ggc cgg cag ccg gcc tcc ttg     1470
Gln Leu Lys Leu Ser Ser Cys Pro Ser Gly Arg Gln Pro Ala Ser Leu
            265                 270                 275

ctg gat gtg cgc tcc gtg cca ggc ctg gac gga tct ggc tgg gag gtg     1518
Leu Asp Val Arg Ser Val Pro Gly Leu Asp Gly Ser Gly Trp Glu Val
        280                 285                 290

ttc gac atc tgg aag ctc ttc cga aac ttt aag aac tcg gcc cag ctg     1566
Phe Asp Ile Trp Lys Leu Phe Arg Asn Phe Lys Asn Ser Ala Gln Leu
    295                 300                 305

tgc ctg gag ctg gag gcc tgg gaa cgg ggc agg gcc gtg gac ctc cgt     1614
Cys Leu Glu Leu Glu Ala Trp Glu Arg Gly Arg Ala Val Asp Leu Arg
310                 315                 320                 325

ggc ctg ggc ttc gac cgc gcc gcc cgg cag gtc cac gag aag gcc ctg     1662
Gly Leu Gly Phe Asp Arg Ala Ala Arg Gln Val His Glu Lys Ala Leu
                330                 335                 340

ttc ctg gtg ttt ggc cgc acc aag aaa cgg gac ctg ttc ttt aat gag     1710
Phe Leu Val Phe Gly Arg Thr Lys Lys Arg Asp Leu Phe Phe Asn Glu
            345                 350                 355

att aag gcc cgc tct ggc cag gac gat aag acc gtg tat gag tac ctg     1758
Ile Lys Ala Arg Ser Gly Gln Asp Asp Lys Thr Val Tyr Glu Tyr Leu
        360                 365                 370

ttc agc cag cgg cga aaa cgg cgg gcc cca ctg gcc act cgc cag ggc     1806
Phe Ser Gln Arg Arg Lys Arg Arg Ala Pro Leu Ala Thr Arg Gln Gly
    375                 380                 385

aag cga ccc agc aag aac ctt aag gct cgc tgc agt cgg aag gca ctg     1854
Lys Arg Pro Ser Lys Asn Leu Lys Ala Arg Cys Ser Arg Lys Ala Leu
390                 395                 400                 405

cat gtc aac ttc aag gac atg ggc tgg gac gac tgg atc atc gca ccc     1902
His Val Asn Phe Lys Asp Met Gly Trp Asp Asp Trp Ile Ile Ala Pro
                410                 415                 420
```

-continued ctt gag tac gag gct ttc cac tgc gag ggg ctg tgc gag ttc cca ttg 1950
Leu Glu Tyr Glu Ala Phe His Cys Glu Gly Leu Cys Glu Phe Pro Leu
425 430 435 cgc tcc cac ctg gag ccc acg aat cat gca gtc atc cag acc ctg atg 1998
Arg Ser His Leu Glu Pro Thr Asn His Ala Val Ile Gln Thr Leu Met
440 445 450 aac tcc atg gac ccc gag tcc aca cca ccc acc nnn tgt gtg ccc acg 2046
Asn Ser Met Asp Pro Glu Ser Thr Pro Pro Thr Xaa Cys Val Pro Thr
455 460 465 cgg ctg agt ccc atc agc atc ctc ttc att gac tct gcc aac aac gtg 2094
Arg Leu Ser Pro Ile Ser Ile Leu Phe Ile Asp Ser Ala Asn Asn Val
470 475 480 485 gtg tat aag cag tat gag gac atg gtc gtg gag tcg tgt ggc tgc agg 2142
Val Tyr Lys Gln Tyr Glu Asp Met Val Val Glu Ser Cys Gly Cys Arg
490 495 500 tagcagcact ggccctctgt cttcctgggt ggcacatccc aagagcccct tcctgcactc 2202 ctggaatcac agaggggtca ggaagctgtg gcaggagcat ctacacagct tgggtgaaag 2262 gggattccaa taagcttgct cgctctctga gtgtgacttg ggctaaaggc cccctttat 2322 ccacaagttc ccctggctga ggattgctgc ccgtctgctg atgtgaccag tggcaggcac 2382 aggtccaggg agacagactc tgaatgggac tgagtcccag gaaacagtgc tttccgatga 2442 gactcagccc accatttctc ctcacctggg ccttctcagc ctctggactc tcctaagcac 2502 ctctcaggag agccacaggt gccactgcct cctcaaatca catttgtgcc tggtgacttc 2562 ctgtccctgg gacagttgag aagctgactg ggcaagagtg ggagagaaga ggagagggct 2622 tggatagagt tgaggagtgt gaggctgtta gactgttaga tttaaatgta tattgatgag 2682 ataaaaagca aaactgtgcc t 2703

<210> SEQ ID NO 2
<211> LENGTH: 501
<212> TYPE: PRT
<213> ORGANISM: Homo sapiens
<220> FEATURE:
<221> NAME/KEY: misc_feature
<222> LOCATION: (465)..(465)
<223> OTHER INFORMATION: The 'Xaa' at location 465 stands for Lys, Asn, Arg, Ser, Thr, Ile, Met, Glu, Asp, Gly, Ala, Val, Gln, His, Pro, Leu, Tyr, Trp, Cys, or Phe.

<400> SEQUENCE: 2

Met Arg Leu Pro Lys Leu Leu Thr Phe Leu Leu Trp Tyr Leu Ala Trp
1 5 10 15

Leu Asp Leu Glu Phe Ile Cys Thr Val Leu Gly Ala Pro Asp Leu Gly
20 25 30

Gln Arg Pro Gln Gly Thr Arg Pro Gly Leu Ala Lys Ala Glu Ala Lys
35 40 45

Glu Arg Pro Pro Leu Ala Arg Asn Val Phe Arg Pro Gly Gly His Ser
50 55 60

Tyr Gly Gly Gly Ala Thr Asn Ala Asn Ala Arg Ala Lys Gly Gly Thr
65 70 75 80

Gly Gln Thr Gly Gly Leu Thr Gln Pro Lys Lys Asp Glu Pro Lys Lys
85 90 95

Leu Pro Pro Arg Pro Gly Gly Pro Glu Pro Lys Pro Gly His Pro Pro
100 105 110

Gln Thr Arg Gln Ala Thr Ala Arg Thr Val Thr Pro Lys Gly Gln Leu
115 120 125

-continued

```
Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
    450                 455                 460

Xaa Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500
```

<210> SEQ ID NO 3
<211> LENGTH: 15
<212> TYPE: PRT
<213> ORGANISM: Artificial Sequence
<220> FEATURE:
<223> OTHER INFORMATION: consensus sequence -continued
<220> FEATURE:
<221> NAME/KEY: REPEAT
<222> LOCATION: (3)..(3)
<223> OTHER INFORMATION: Xaa=(Y)25-29 with Y=any amino acid including cysteine
<220> FEATURE:
<221> NAME/KEY: VARIANT
<222> LOCATION: (5)..(7)
<223> OTHER INFORMATION: Xaa=Y with Y=any amino acid including cysteine
<220> FEATURE:
<221> NAME/KEY: REPEAT
<222> LOCATION: (9)..(9)
<223> OTHER INFORMATION: Xaa=X with X=any amino acid except cysteine
<220> FEATURE:
<221> NAME/KEY: VARIANT
<222> LOCATION: (10)..(10)
<223> OTHER INFORMATION: Xaa=X wtih X=any amino acid except cysteine
<220> FEATURE:
<221> NAME/KEY: REPEAT
<222> LOCATION: (12)..(12)
<223> OTHER INFORMATION: Xaa=(Y)27-34 with Y=any amino acid including cysteine
<220> FEATURE:
<221> NAME/KEY: VARIANT
<222> LOCATION: (14)..(14)
<223> OTHER INFORMATION: Xaa=Y with Y=any amino acid including cysteine

<400> SEQUENCE: 3

```
Cys Cys Xaa Cys Xaa Xaa Xaa Cys Xaa Xaa Cys Xaa Cys Xaa Cys
1               5                   10                  15
```

<210> SEQ ID NO 4
<211> LENGTH: 14
<212> TYPE: PRT
<213> ORGANISM: Artificial Sequence
<220> FEATURE:
<223> OTHER INFORMATION: consensus sequence
<220> FEATURE:
<221> NAME/KEY: REPEAT
<222> LOCATION: (2)..(2)
<223> OTHER INFORMATION: Xaa=(Y)28 with Y=any amino acid including cysteine
<220> FEATURE:
<221> NAME/KEY: VARIANT
<222> LOCATION: (4)..(6)
<223> OTHER INFORMATION: Xaa=Y wtih Y=any amino acid including cysteine
<220> FEATURE:
<221> NAME/KEY: REPEAT
<222> LOCATION: (8)..(8)
<223> OTHER INFORMATION: Xaa=(Y)30-32 with Y=any amino acid including cysteine
<220> FEATURE:
<221> NAME/KEY: VARIANT
<222> LOCATION: (9)..(9)
<223> OTHER INFORMATION: Xaa=X with X=any amino acid except cysteine
<220> FEATURE:
<221> NAME/KEY: REPEAT
<222> LOCATION: (11)..(11)
<223> OTHER INFORMATION: Xaa=(Y)31 with Y=any amino acid including cysteine
<220> FEATURE:
<221> NAME/KEY: VARIANT
<222> LOCATION: (13)..(13)
<223> OTHER INFORMATION: Xaa=Y with Y=any amino acid including cysteine

<400> SEQUENCE: 4

```
Cys Xaa Cys Xaa Xaa Xaa Cys Xaa Xaa Cys Xaa Cys Xaa Cys
1               5                   10
```

<210> SEQ ID NO 5
<211> LENGTH: 13
<212> TYPE: PRT
<213> ORGANISM: Artificial Sequence
<220> FEATURE:
<223> OTHER INFORMATION: consensus sequence -continued
<220> FEATURE:
<221> NAME/KEY: REPEAT
<222> LOCATION: (2)..(2)
<223> OTHER INFORMATION: Xaa=(X)28 with X=any amino acid except cysteine
<220> FEATURE:
<221> NAME/KEY: VARIANT
<222> LOCATION: (4)..(6)
<223> OTHER INFORMATION: Xaa=X with X=any amino acid except cysteine
<220> FEATURE:
<221> NAME/KEY: REPEAT
<222> LOCATION: (8)..(8)
<223> OTHER INFORMATION: Xaa=(X)31-33 with X=any amino acid except
cysteine
<220> FEATURE:
<221> NAME/KEY: REPEAT
<222> LOCATION: (10)..(10)
<223> OTHER INFORMATION: Xaa=(X)31 with X=any amino acid except cysteine
<220> FEATURE:
<221> NAME/KEY: VARIANT
<222> LOCATION: (12)..(12)
<223> OTHER INFORMATION: Xaa=X with X=any amino acid except cysteine

<400> SEQUENCE: 5

Cys Xaa Cys Xaa Xaa Xaa Cys Xaa Cys Xaa Cys Xaa Cys
1 5 10

OSTEOINDUCTIVE MATERIALS

CROSS REFERENCE TO RELATED APPLICATION

Figure 1:
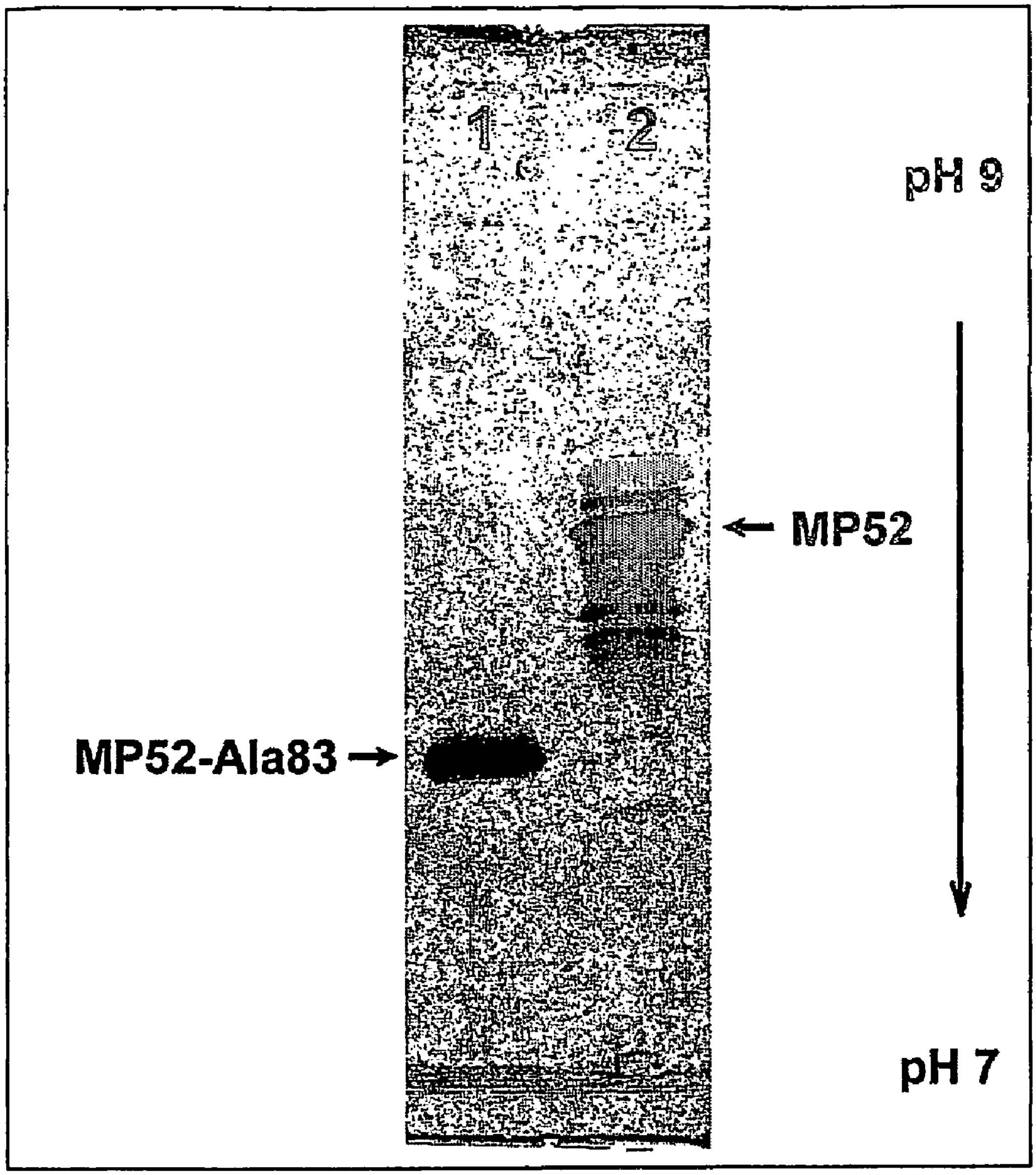

This application is a 35 USC § 371 National Phase Entry Application from PCT/EP2004/003238, filed Mar. 26, 2004, and designating the United States.

The present invention concerns improved osteoinductive materials comprising matrix materials and morphogenetic proteins, wherein depending on the subject matter the proteins may be dimeric or monomeric proteins. The osteoinductive materials according to the present invention have improved properties. The invention further concerns methods for producing the respective improved osteoinductive materials.

Many growth factors of the TGF-β superfamily (Kingsley, Genes and Development 8, 133-146 (1994) as well as the references cited therein) are relevant for a wide range of medical treatment methods and applications which in particular concern promotion of cell proliferation and tissue formation, including wound healing and tissue reproduction. Such growth factors in particular comprise members of the TGF-β (transforming growth factor, cf. e.g. Roberts and Spom, Handbook of Experimental Pharmacology 95 (1990), page 419-472, editors: Spom and Roberts), the DVR-group (Hötten et al., Biochem. Biophys. Res. Comm., 206 (1995), page 608-613 and further literature cited therein) including BMPs (bone morphogenetic protein, cf. e.g. Rosen and Thies, Growth Factors in Perinatal Development (1993), page 39-58, editors: Tsang, Lemons and Balistreri) and GDFs (growth differentiation factors), the inhibin/activin (cf. e.g. Vale et al., The Physiology of Reproduction, second edition (1994), page 1861-1878, editors: Knobil and Neill) and the GDNF protein family (Rosenthal, Neuron 22 (1999), page 201-203; Airaksinen et al. Mol Cell Neurosci 13 (1999), page 313-325). Although the members of the TGF-β superfamily show high amino acid homologies in the mature part of the protein, in particular 7 conserved cysteines, they show considerable variations in their exact functions. Often individual growth factors of these families exhibit a plurality of functions at the same time, so that their application is of interest in various medical indications. Some of these multifunctional proteins also have survival promoting effects on neurons in addition to functions such as e.g. regulation of the proliferation and differention in many cell types (Roberts and Spom, supra; Sakurai et al., J. Biol. Chem. 269 (1994), page 14118-14122). Thus e.g. trophic effects on embryonic motoric and sensory neurons were demonstrated for TGF-β in vitro (Martinou et al., Dev. Brain Res. 52, page 175-181 (1990) and Chalazonitis et al., Dev. Biol. 152, page 121-132 (1992)). In addition, effects promoting survival of dopaminergic neurons are shown for TGF-β-1, -2, -3, activin A and GDNF, a protein which has structural similarities to TGF-β superfamily members. (Krieglstein et al., EMBO J. 14, page 736-742 (1995))

The occurrence of proteins of the TGF-β superfamily in various tissuous stages and development stages corresponds with differences with regard to their exact functions as well as target sites, life span, requirements for auxiliary factors, necessary cellular physiological environment and/or resistance to degradation.

The proteins of the TGF-β superfamily exist as homodimers or heterodimers having a single disulfide bond in nature. However, it was discovered that also proteins lacking the cysteine responsible for dimer formation maintain the characteristic properties of the dimeric wild-type proteins at least to a substantial extent. Such forms may have advantages over the dimeric proteins, especially when ease of production, i.e. reproducible, simple and inexpensive production by genetic engineering methods is concerned. Examples for such proteins and their production as well as their use are described in WO01/11041.

Mainly for applications in the bone related field, like e.g. repair of bone defects or bone regeneration, filling in of bone defects caused by disease, trauma or operation or degenerative bone defects etc., but also for cartilage, connective tissue such as tendon or ligament, dental, neurological, angiogenetic or other applications it is useful to combine morphogenetic proteins with matrix materials. Such matrix materials which are coated or soaked with morphogenetic proteins can provide a device for continuous release of morphogenetic protein and therefore constant stimulation of progenitor cells to differentiate and form new cells of the damaged kind of tissue. Additionally the matrix material may provide a favourable environment for adhesion and ingrowth of proliferating cells and thereby accelerate formation of new tissue, especially bony tissue.

Such uses of morphogenetic proteins in combination with matrix materials are extensively published and described, such as for example in WO98/21972. However there is still a need for materials which contain high amounts of morphogenetic proteins in a form which provides continuous release of protein. Homogeneous and maximal coating of matrix materials with morphogenetic proteins is a crucial factor for successful osteoinductive materials and is still an object to be solved. One main problem is the limited solubility of morphogenetic proteins. State of the art osteoinductive materials often contain only small amounts of active morphogenetic proteins because the proteins are unstable or bound nonuniformously to the matrix surfaces. Especially inner surfaces of porous matrix materials are coated insufficiently.

It was therefore an object of the present invention to provide improved osteoinductive materials for use in the pharmaceutical field and especially to provide methods to obtain matrix materials which are efficiently coated with morphogenetic proteins.

This issue is solved according to the present invention by providing osteoinductive materials as described herein and in the attached claims.

In order to avoid misunderstandings and ambiguities, some frequently used terms herein are defined and exemplified as follows:

The term "morphogenetic protein" as used herein means a protein of the TGF-β superfamily or a biologically active part or variant thereof. This term comprises all proteins which contain at least a 7 cysteine region characteristic for TGF-β superfamily proteins, regardless whether the cysteine responsible for dimer formation present in this domain has been replaced by another amino acid or not. Interesting members of the TGF-β superfamily or biologically active parts or variants thereof are e.g. the TGF-β proteins like TGF-β1, TGF-β2, TGF-β3, TGF-β4, TGF-β5 (U.S. Pat. No. 5,284,763; EP 0376785; U.S. Pat. No. 4,886,747; DNA 7 (1988), page 1%), EMBO J. 7 (1988), page 3737-3743), Mol. Endo. 2 (1988), page 1186-1195), J. Biol. Chem. 265 (1990), page 1089-1093), OP1, OP2 and OP3 proteins (U.S. Pat. No. 5,011,691, U.S. Pat. No. 5,652,337, WO 91/05802) as well as BMP2, BMP3, BMP4 (WO 88/00205, U.S. Pat. No. 5,013,649 and WO 89/10409, Science 242 (1988), page 1528-1534), BMP5, BMP6 and BMP-7 (OP1) (Proc. Nat. Acad. Sci. 87 (1990), page 9841-9847, WO 90/11366), BMP8 (OP2) (WO 91/18098), BMP9 (WO 93/00432), BMP10 (WO 94/26893), BMP11 (WO 94/26892), BMP12 (WO 95/16035), BMP13 (WO95/16035), BMP15 (WO 96/36710), BMP16 (WO 98/12322), BMP3b (Biochem. Biophys. Res. Comm. 219 (1996), page 656-662), GDF1 (WO 92/00382 and Proc. Natl. Acad. Sci. 88 (1991), page 4250-4254), GDF8 (WO 94/21681), GDF10 (WO095/10539), GDF11 (WO 96/01845), GDF5 (CDMP1, MP52) (WO 95/04819; WO96/01316; WO 94/15949, WO 96/14335 and WO 93/16099 and Nature 368 (1994), page 639-643), GDF6 (CDMP2, BMP13) (WO 95/01801, WO 96/14335 and WO95/16035), GDF7 (CDMP3, BMP12) (WO 95/01802 and WO 95/10635), GDF14 (WO 97/36926), GFD15 (WO 99/06445), GDF16 (WO 99/06556), 60A (Proc. Natl. Acad. Sci. 88 (1991), page 9214-9218), DPP (Nature 325 (1987), page 81-84), Vgr-1 (Proc. Natl. Acad. Sci. 86 (1989), page 4554-4558) Vg-1, (Cell 51 (1987), page 861-867), dorsalin (Cell 73 (1993), page 687-702), MIS (Cell 45 (1986), page 685-698), pCL13 (WO 97/00958), BIP (WO 94/01557), inhibin a, activin βA and activin βB (EP 0222491), activin BC (MP121) (WO 96/01316), activin βE and GDF12 (WO 96/02559 and WO 98/22492), activin βD (Biochem. Biophys. Res. Comm. 210 (1995), page 581-588), GDNF (Science 260 (1993), page 1130-1132, WO 93/06116), Neurturin (Nature 384 (1996), page 467-470), Persephin (Neuron 20 (1998), page 245-253, WO 97/33911), Artemin (Neuron 21 (1998), page 1291-1302), Mic-1 (Proc. Natl. Acad. Sci. USA 94 (1997), page 11514-11519), Univin (Dev. Biol. 166 (1994), page 149-158), ADMP (Development 121 (1995), page 4293-4301), Nodal (Nature 361 (1993), page 543-547), Screw (Genes Dev. 8 (1994), page 2588-2601). Furthermore, also non naturally occurring and therefore artificially produced proteins of the TGF-β superfamily are included in the term "morphogenetic proteins", such as e.g. proteins of the TGF-β superfamily lacking a cysteine responsible for dimer formation as e.g. described in WO 01/11041, which occur preferably as monomeric proteins or only in weak association with a further monomer due to non covalent association like hydrogen bounding. Other useful proteins also included in the definition "morphogenetic protein" are biologically active biosynthetic constructs including biosynthetic proteins designed using sequences from two or more known morphogenetic proteins. Examples of biosynthetic constructs are disclosed in U.S. Pat. No. 5,011,691 (e.g. COP-1, COP-3, COP-4, COP-5, COP-7 and COP-16). The disclosure of the cited publications including patents or patent applications are incorporated herein by reference. Most of the members of the TGF-β protein superfamily are morphogenetic proteins that are useful for treatments where regulation of differentiation and proliferation of cells or progenitor cells is of interest. This can result in replacement of damaged and/or diseased issue like for example skeletal (bone, cartilage) tissue, connective tissue, periodontal or dental tissue, neural tissue, tissue of the sensory system, liver, pancreas, cardiac, blood vessel, skin and renal tissue, uterine or thyroid tissue etc. Morphogenetic proteins are often useful for the treatment of ulcerative or inflammatory tissue damage and wound healing of any kind such as enhanced healing of ulcers, burns, injuries or skin grafts.

The term biologically active part or variant thereof as used herein means protein fragments retaining activity, precursor proteins that are e.g. cleaved at the site of activity to the mature form or show biological activity themselves, or also protein variants that still maintain essentially the biological activity of the wild-type protein. Such variants preferably contain conservative amino acid substitutions, but especially at the N-terminal part of the mature proteins even considerable deletions or substitutions do not lead to a considerable loss of biological activity. Persons skilled in the art are well able to determine whether a certain protein shows the required biological activity. Proteins showing at least 70% and preferably at least 80% homology to the mature wild-type proteins should be understood as encompassed by the present invention.

The term "homology" as used herein means that amino acids within the following groups are considered homologous: "S, T, P, A, G" and "N, Q, D, E" and "H, R, K" and "M, I, L, V" and "F, Y, W", wherein homology is determined using an alignment for optimal sequence correspondence, including gaps where applicable.

The term "matrix material" as used herein means a carrier matrix acting as a scaffold for recruitment, attachment, infiltration, proliferation and differentiation of cells and/or as a potential delivery and storage device for morphogenetic proteins. All types of matrix materials are useful in accordance with the present invention, as long as they are biocompatible and selected for the intended area or indication of use. The matrix material can be a natural material, a modified natural material as well as a synthetic material. All already known matrices for morphogenetic proteins are encompassed. Examples of natural materials are e.g. autologous, heterologous or xenologous bone materials, collagen, e.g. collagen type I and III, or metals like titanium. Also other components of the extracellular matrix can be used. The extracellular matrix comprises for example the various collagens, as for example types I, II, V, IX, X, XI and XIII, further hydroxyl apatite, proteoglycanes and glycosaminoglycanes, as for example chondroitinsulfate, biglycane, decorine and/or hyaluronic acid, or noncollagenous proteins as for example osteopontin, laminin, fibronectin, vitronectin, thrombospondin, cartilage matrix protein and dentin phosphoprotein. All mentioned natural materials may also be used in artificially modified forms.

Examples of modified natural materials are demineralized bone, thermoashed bone mineral, sintered bone or chemically crosslinked hyaluronic acid (hydrogel), or metal alloys.

Examples of synthetic materials are polymers like polyglycolic acid, polylactide and polylactide derivatives such as e.g. polylactic add, poly(lactide-co-glycolide), polylactid acid-polyethylene glycol or glycolide L-lactide copolymers, further polyphosphates, polyethylene glycol, polyoxyethylene polyoxypropylene copolymers or materials containing calcium phosphates such as beta-tricalcium phosphate ($Ca_3(PO_4)_2$), alpha-tricalcium phosphate and hydroxyl apatite.

Further examples of other useful carrier matrices belonging to one of the above mentioned groups are $Ca(OH)_2$, coral, natural bone mineral, chitin, non-demineralized bone particles, ceramic bone particles, ceramic dentin, irradiated cancellous bone chips, plaster of Paris, bioactive glass, apatite-wollastonite-containing glass ceramic. Also a combination of the above mentioned carrier matrices can form the matrix material as for example the combination of hydroxy apatite and collagen (e.g. Healos, previously available from Orquest, Inc., CA, USA, [now DePuy Acromed, MA, USA]), a combination of polyglycolic acid and polylactic acid or polylactid derivatives, or coral-collagen composites. For a non limiting list of useful carrier matrices see further Kirker-Head, Advanced Drug Delivery 43 (2000), page 65-92.

The term "osteoinductive material" as used herein means a biological device comprising at least a matrix material and a morphogenetic protein temporarily immobilized within and/or on the surface of said matrix material. Furthermore, the device may comprise additives that are useful for the envisaged application. Such substances include for example, but are not limited to antibiotics, antifibrinolytic agents, vitamins, stabilizers, buffers, emulgators, antinflammatory substances or other additives, like for example substances, which enhance the solubility of the morphogenetic protein. It is a prerequisite for such substances that they are not harmful to the patient and do not disturb the intended pharmaceutical application. The term “osteoinductive material” according to the present invention is not meant to be limited to the use in the area of bone repair. Also for other indications, such as for example for the repair or growth of cartilage, connective tissue including tendon and/or ligament, periodontal or dental tissue, neural tissue, tissue of the sensory system, liver, pancreas, cardiac, blood vessel, renal, uterine, and thyroid tissue, skin, mucous membranes, endothelium, epithelium, for promotion or induction of nerve growth, tissue repair and regeneration, angiogenesis, wound healing including ulcers, burns, injuries or skin grafts, induction of proliferation of progenitor cells or bone marrow cells, the use of a combination of protein and matrix material can be useful to e.g. take advantage of slow continuous release of protein and/or providing an environment that enables cells to grow in and thus support formation of new healthy tissue. Rather the term “osteoinductive material” is used because of the meaning it has already acquired in the state of the art as combination of matrix materials and morphogenetic proteins. The osteoinductive materials according to the invention are useful in all instances where morphogenetic proteins are beneficially applied, and especially where morphogenetic proteins are applied together with a matrix material to provide for slow and sustained release of protein and/or to provide an environment that further facilitates and enhances cell proliferation and tissue regeneration. The osteoinductive material according to the invention can for example be used for preventing, alleviating or treating symptoms or conditions of diseases or abnormal conditions of cartilage, bone, connective tissue including tendon and/or ligament, periodontal or dental tissue, neural tissue, tissue of the sensory system, liver, pancreas, cardiac, blood vessels, renal, uterine and thyroid tissue, skin, mucous membranes, endothelium or epithelium. The materials can be used but are not limited to promotion or induction of nerve growth, tissue repair and regeneration, angiogenesis, wound healing including ulcers, burns, injuries or skin grafts, induction of proliferation of progenitor cells or bone marrow cells, for regeneration of functional attachment between connective tissue and bone, cartilage repair, treatment of osteoporosis or osteoarthritis, to correct non-union fractures, acquired or congenital craniofacial, skeletal or dental abnormalities, for non-skeletal tissue replacement in plastic or reconstructive surgery. Further, the disease or abnormal condition to be treated by the osteoinductive material can be caused by ischemic or traumatic injury, degenerative disease, cardiomyopathies, atherothrombotic or cardioembolic strokes, ulceration, cirrhosis, emphysema, cell senescence or quiescence.

Further, the osteogenic material can be used for modulating of an inflammatory response and alleviating the tissue destructive effects associated therewith and for enhancing the viability of damaged or injured tissue. Further, the alleviation of fibrosis or scar issue formation can be avoided and the material can be used beneficially for treating ischemic-repair fusion injuries like associated with a cardiac arrest, pulmonary occlusion, arterial occlusion, coronary occlusion or occlusive stroke, associated with a surgery or other necessary interruption of blood flow, or associated with a cerebral infarction, myocardial infarction, asphyxia or cardiopulmonary arrest. A further possible indication is healing and repair of connective tissue attachment like for example described in WO 96/39169. The possible indications for using osteogenic material according to the invention is only exemplary and not intended to limit the invention thereto. The osteoinductive materials according to the present invention contain a maximal dosage of morphogenetic proteins in a biologically active and effective form in and/or on the surfaces of the preferably porous matrix material.

The terms “evenly coated” and “evenness of coating” as used herein mean that each $mm^2$ of the surface of the osteoinductive material contains basically equal amounts of morphogenetic proteins.

Osteoinductive materials described in the art often exhibit an uneven distribution of the bioactive morphogenetic proteins on the carrier. In most of these cases either less protein is being bound on some parts of the matrix or a considerable percentage of the bound protein displays reduced bioactivity. According to the present invention it has been found that this unevenness is mainly influenced by local precipitation events which take place during the coating of the matrix materials together with protein degradation processes. Thus, the osteoinductive capability of the device is significantly reduced. Such uneven distribution and protein degradation can be avoided by modifying or enhancing both protein stability and solubility during the coating process, which is attainable by skilful selection and control of the pH conditions as well as by the use of the suitable buffer or solvent characteristics and specific additives.

The solubility of morphogenetic proteins in liquids depends, besides other important factors also disclosed herein, upon the pH value of the solvent. Coating of a matrix material with morphogenetic proteins is most efficient, if the proteins are completely dissolved within the coating solution in a stable manner during the whole term of the coating procedure. However, since most matrix materials are either donators or acceptors of hydrogen ions, the matrix materials themselves affect the pH during the coating process. The surface of most matrix materials is maximized and contains countless cavities and pores, which exhibit local microenvironments with sometimes different pH conditions, where the proteins tend to precipitate. The methods of the present invention allow the protein solution to distribute evenly across the outer and inner surface of the carrier material and to bind homogenously and stably to these surfaces without the risk of a pH-induced precipitation of the protein.

This evenness of coating and especially the effective adsorption of morphogenetic proteins to the matrix material, according to the present invention, is therefore achieved by providing the proteins stably and completely dissolved in a solution. In general, the solvent for the morphogenetic proteins used within the coating procedure has to stabilize the proteins and to compensate critical pH shifts caused by the carrier. According to this invention, exact knowledge of the pH-dependent solubility of the morphogenetic proteins together with a basic knowledge of the matrix characteristics allows to choose a suitable solvent or buffer for the coating procedure. For example, if the morphogenetic proteins are soluble at a pH less than 4.5 but precipitate at higher pH values, and the matrix material itself has alkaline properties, the solvent or buffer used within the coating procedure should contain suitable substances, preferably a weak acid, to compensate for the pH shift caused by the carrier in order to keep the morphogenetic proteins efficiently in solution during the whole coating process. If the morphogenetic proteins are soluble at a pH above 10 but precipitate at lower pH values, and the matrix material itself has acidic properties, the solvent or buffer used within the coating procedure should contain other suitable substances, preferably a weak base, for efficient compensation. Examples describing the influence of different matrices on the pH as well as the pH-dependent solubilities of several morphogenetic proteins are given herein. According to the other embodiments of the present invention which are not explicitely exemplified, a person skilled in the art is well able to easily determine the influence of any other matrix on the pH as well as the specific pH-dependent solubility for any other morphogenetic protein.

The morphogenetic proteins of this invention usually precipitate at physiological (nearly neutral) or slightly acidic/basic pH values, whereas they are soluble at pH values below 4.5 and above 10.3, if the solvents exhibit ionic concentrations of 100 mmol/l or more. Surprisingly this pH-dependent solubility of the morphogenetic proteins can be additionally modified by changing the composition or concentration of the buffers or solvents, therefore leading to a clearly enlarged pH range in which an even and stable coating of matrix materials is possible. In solvents with lower ionic concentrations such as e.g. 10 or 20 mmol/l, protein solubilities of at least 75 μg/ml, preferably 100 μg/ml, more preferably 150 μg/ml and most preferably more than 200 μg/1 ml are achievable at pH values below 5.2 and above 9.5. This enlarged pH range is especially favourable if pH-sensitive matrices, e.g. matrices comprising natural materials, are coated.

According to this aspect of the invention, the pH-dependent solubility of the morphogenetic protein and the stable coating of the matrix material is dependent upon the ionic concentration of the buffer or solvent used and can be strongly improved by using a buffer or solvent of low ionic concentration. Preferably, said buffer or solvent has an ionic concentration of 150 mmol/l or less, preferably 100 mmol/l or less, 80 mmol/l or less, 40 mmol/l or less, 20 mmol/l or less, 10 mmol/l or less, or 5 mmol/l or less. More preferably, the buffer or solvent has a concentration of 20 mmol/l. Most preferably, the buffer or solvent has a concentration of 10 mmol/l.

It has furthermore been found that also the solvent composition influences the pH-dependent solubility of the morphogenetic protein and the stable coating of the matrix material. Whereas buffers containing either sodium citrate, 2-amino-2-methyl-1,3-propanediol-HCl or sodium glycine have been proven to be less suited as solvents for the morphogenetic proteins, remarkable good protein stability or solubility has been obtained in solvents containing sodium acetate, sodium carbonate or in unbuffered solutions containing HCl or NaOH. Additionally, good protein solubility has unexpectedly been found in solutions comprising organic solvents such as trifluoroacetic acid (TFA), TFA/ethanol compositions, isopropanol, propanol, butanol, isopropanol, dimethyl sulfoxide or aceton.

According to this aspect of the present invention, the buffer or solvent for the morphogenetic proteins contains preferably an acid such as e.g. acetic acid or hydrochloric acid or a base such as e.g. NaOH. More preferably, the solvent is a buffer containing sodium acetate or sodium carbonate. Also preferably, the solvent contains more than 25%, 30%, 40%, 50%, 75%, or even 100% organic solvents.

It was additionally quite unexpected that the morphogenetic proteins are not solely soluble but also maintain their biological activity at strongly acidic (below pH 5.2) as well as at strongly basic pH values (above pH 9.5) which rarely occur under physiological conditions. These results allow the development of specific matrix materials and coating methods thereof. Solutions of active morphogenetic proteins having these extreme pH values are supporting sterility. Because of this they can be used advantageously within the coating procedure since the danger of an undesired contamination with viable microorganisms is significantly reduced. On top of that, coating at e.g. basic pH between 9.5 and 12 is in some cases beneficial because several matrices degrade in acidic milieus and therefore need basic pH conditions during the coating. Furthermore, coating of matrix materials which have neutral or basic properties by themselves can be performed at high pH values and generally excludes the risk of precipitation of the protein during the coating procedure.

For example, $Ca(OH)_2$ is a material routinely used in tooth repair procedures but exhibits a pH value of about 12 in aqueous solutions, which normally prevents a coating with proteins. $Ca(OH)_2$ has been previously shown to stimulate the formation of minor amounts of secondary dentin. This effect can be dramatically enhanced by coating of the $Ca(OH)_2$ at pH12 with the morphogenetic proteins according to this invention.

The data summarized above enable, in a specific embodiment of the present invention, a coating of matrix materials with biologically active morphogenetic proteins at pH values below pH 5.2 and at particularly high pH between 9.5 and 13. Preferred are pH values between 12 and 13. Especially preferred are pH values between 2 and 4.5, between 4.5 and 5.2, between 9.5 and 10.3 and between 10.3 and 12. and between 12 and 13.

The coating of a matrix material can be furthermore strongly improved by using stabilizers, emulgators and other auxiliaries and additives which e.g. prevent their degradation or enhance their solubility. Especially preferred are polyethylene glycols which dramatically enhance the solubility of the morphogenetic proteins if covalently or noncovalently bound to the proteins. Other useful additives and auxiliaries can be substances that are e.g. beneficial for the uniform adsorption of protein on matrix material as well as substances that stabilize the protein in solution. Furthermore any substance may be included, as long as it has a positive effect in any way or is at least not harmful for the patient. Examples for useful substances are nonionic detergents like Tween80, basic amino acids, carrier proteins like serum albumin, alkaline salts of fatty acids (soaps) or syndets (synthetic detergents other than soaps), sugars or alcohols like e.g. sucrose, mannitol (WO98/33514), ethanol or isopropanol. Especially sugars and alcohols as well as soaps and syndets have been found to improve the evenness of the coating. These solutions containing alcohols, soaps and/or syndets are very advantageous because of their very low surface tension, which improves the effectivity of coating. In injectable matrix materials and formulations useful for parenteral administration, soaps and syndets are helpful because they form micellar structures. Those micelles are capable of surrounding and emulsifying the hydrophobic morphogenetic proteins, thereby supporting protein delivery and preventing precipitation. Since soaps have basic properties with pH values above 8, they can be easily combined with the morphogenetic proteins of the present invention, which have been proven to remain biologically active at those basic pH values. In the acidic pH range below 5.2, syndets instead of soaps can be used in combination with the morphogenetic proteins. Also other substances like antibiotics, antiseptics, vitamins, anti-fibrinolytics etc. can be added if desired.

In detail, the coating of a matrix material can be strongly improved according to the present invention by using one or more saccharides as additives. Preferably, said saccharide is sucrose. Also preferably, said saccharide is mannitol. Especially preferred are coating solutions which include up to 8%, 10%, 12%, 15% or 20% saccharides.

Additionally, the coating of a matrix material can be strongly improved by using one or more alcohols as additives. Preferably, said alcohol is ethanol. Also preferably, said alcohol is isopropanol. Especially preferred are coating solutions which include up to 50%, 55%, 60% or 65% alcohols.

Furthermore, the coating of a matrix material as well as the composition of injectable carriers or parentaral formulations of the morphogenetic proteins can be improved by using alkaline salts of fatty acids (soaps) as additives. Preferably, said soap is sodium stearate, sodium myristate, sodium oleate or sodium palmeate. Especially preferred are solutions which include up to 10%, 20%, 30%, 40%, 50% or 75% soaps.

The coating of a matrix material as well as the composition of an injectable or parenteral formulation of the morphogenetic proteins can be also improved by using alkaline salts of syndets as additives. Preferably, said syndet is an linear alkyl sulfonate, an alkyl sulfuate, or an alkyle benzene sulfonate. More preferably, said syndet is an laurel or laureth sulfate. Most preferably, said syndet is sodium or ammonium lauryl sulfate. Especially preferred are solutions which include up to 10%, 20%, 30%, 40%, 50% or 75% syndets.

One aspect of the present invention provides an osteoinductive material comprising a matrix material and adsorbed on outer or inner surfaces of this matrix material one or more morphogenetic protein(s), wherein the osteoinductive material is obtainable by contacting the matrix material and the morphogenetic protein under suitable conditions to keep the protein dissolved in a solution thereby allowing that the matrix material is evenly coated with the morphogenetic protein. This matrix material is acting as a scaffold for cell recruitment, attachment, proliferation and/or differentiation and as a potential delivery and storage device for morphogenetic proteins. In a preferred embodiment, the matrix material is a porous material and allows penetration of a solution of the protein to the inner surfaces of the material. Also preferably, the matrix material is a natural material, a modified natural material or a synthetic material. Even more preferably, the matrix material contains a type of calcium phosphate, especially beta-tricalcium phosphate ($Ca_3(PO_4)_2$), alpha-tricalcium phosphate and hydroxyl apatite. Also especially preferred are the following matrix materials: a) collagen, b) $Ca(OH)_2$, c) polylactide derivatives: polylactide, polylactic acid, poly(lactide-co-glycolide), polylactid acid-polyethylene glycol, d) hyaluronic acid e) polyoxyethylene polyoxypropylene copolymers. Also especially preferred is a combination of hydroxy apatite and collagen (e.g. Healos, previously available from Orquest, Inc., CA, USA, [now DePuy Acromed, MA, USA]).

The morphogenetic proteins comprised in the osteoinductive material are proteins belonging to the TGF-β superfamily or biologically active parts or variants thereof, which can be dimeric or lack the cysteine responsible for dimer formation.

All TGF-β superfamily members contain a specific domain called "7 cysteine region" This specific 7 cysteine region is considered to be the most important part of the proteins in view of the biological activity. Therefore proteins retaining this critical region are preferred proteins according to the invention. In this region the respective location of the cysteine residues to each other is important and is only allowed to vary slightly in order not to lose the biological activity. Consensus sequences for such proteins are known in the state of the art and all proteins complying with such consensus sequences are considered to be encompassed by the present invention. It is especially preferred that proteins according to this aspect of the invention contain at least the 7 cysteine region characteristic for the TGF-β protein superfamily, regardless weather the cysteine responsible for dimer formation present in this domain has been replaced by another amino acid or not.

In a preferred embodiment the morphogenetic protein or biologically active part or variant thereof is a mature protein or a biologically active part or variant thereof.

Also preferably, the morphogenetic protein or biologically active part or variant thereof is a member of the TGF-β superfamily subgroups called TGF-β, BMP-, GDF-, activin- or GDNF-families.

Several BMP proteins which were originally discovered by their ability to induce bone formation have been described. Meanwhile, several additional functions have been found as it is also true for members of the GDFs. These proteins show a very broad field of applications and especially are in addition to their bone and cartilage growth promoting activity (see for example: WO 88/00205, WO 90/11366, WO 91/05802) useful in periodontal disease, for inhibiting periodontal and tooth tissue loss, for sealing tooth cavities, for enhancing integration of a tooth in a tooth socket (see for example: WO 96/26737, WO 94/06399, WO 95/24210), for connective tissue such as tendon or ligament (see for example: WO 95/16035), for improving survival of neural cells, for inducing growth of neural cells and repairing neural defects, for damaged CNS tissue due to stroke, trauma or degenerative diseases (see for example: WO 97/34626, WO 94/03200, WO 95/05846), for maintaining or restoring sensory perception (see for example WO 98/20890, WO 98/20889), for renal failure (see for example: WO 97/41880, WO 97/41881), for liver regeneration (see for example WO 94/06449), for regeneration of myocardium (see for example WO 98/27995), for treatment or preservation of tissues or cells for organ or tissue transplantation, for integrity of gastrointestinal lining (see for example WO 94/06420), for increasing progenitor cell population as for example hematopoletic progenitor cells by ex vivo stimulation (see for example WO 92/15323) etc.

More preferably, the morphogenetic protein or biologically active part or variant thereof is a dimeric protein belonging to the TGF-β, BMP-, GDF-, activin- or GDNF-families. Even more preferably, the dimeric morphogenetic protein or biologically active part or variant thereof is BMP2, BMP7, BMP12 or BMP13.

Most preferably, the dimeric protein contained in the osteoinductive material according to the invention is protein MP52 (also termed GDF5 or CDMP-1) or a biologically active part or variant thereof. The MP52 sequence is shown in SEQ.ID.NO.1 (DNA and protein sequence) and SEQ.ID.No.2 (protein sequence, only), whereas the Xaa at position 465 represents cysteine. SEQ.ID.NO.2 shows the complete protein sequence of the prepro protein of human MP52 as already disclosed in WO 95/04819. The start of the mature protein lies preferably in the area of amino acids 352-400, especially preferred at amino acids 381 or 382. Therefore, the mature protein comprises amino acids 381-501 or 382-501. The first alanine of the mature protein can be deleted and the mature protein then preferably comprises amino acids 383-501.

Applications for MP52 reflect several of the already described applications for the BMP/GDF family. MP52 is considered to be a very effective promoter of bone and cartilage formation as well as connective tissue formation (see for example WO 95/04819, Hötten et al., (1996), Growth Factors 13, 65-74, Storm et al., (1994) Nature 368, 639-643, Chang et al., (1994) J. Biol. Chem. 269 (45), 28227-28234). In this connection MP52 is useful for applications concerning the joints between skeletal elements (see for example Storm & Kingsley (1996) Development 122, 3969-3979). One example for connective tissue is tendon and ligament (Wolfman et al., (1997), J. Clin. Invest. 100, 321-330, Aspenberg & Forslund (1999), Acta Orthop Scand 70, 51-54, WO 95/16035). MP52 is also useful for tooth (dental and periodontal) applications (see for example WO 95/04819, WO 93/16099, Morotome et al. (1998), Biochem Biophys Res Comm 244, 85-90). MP52 is useful in wound repair of any kind. It is in addition very useful for promoting tissue growth in the neuronal system and survival of dopaminergic neurons, for example. MP52 in this connection is useful for applications in neurodegenerative diseases like e.g. Parkinson's disease and possibly also Alzheimer's disease for Huntington chorea tissues (see for example WO 97/03188, Krieglstein et al., (1995) J. Neurosci Res. 42, 724-732, Sullivan et al., (1997) Neurosci Lett 233, 73-76, Sullivan et al. (1998), Eur. J. Neurosci 10, 3681-3688). MP52 allows to maintain nervous function or to retain nervous function in already damaged tissues. MP52 is therefore considered to be a generally applicable neurotrophic factor. It is also useful for diseases of the eye, in particular retina cornea and optic nerve (see for example WO 97/03188, You et al. (1999), Invest Opthalmol V is Sci 40, 296-311), and for hair growth and the treatment and diagnosis of skin related disorders (WO 02/076494).

Like in the already above mentioned definition of these terms, MP52 can e.g. be used in its mature form, however, it can also be used as a fragment thereof containing at least the 7 cysteine region or also in a precursory form. Deviations at the N-terminal part of mature MP52 do not affect its activity to a considerable degree. Therefore, substitutions or deletions within the first 9 amino adds or additions on the N-terminal part of the proteins are still within the scope of the present invention. It might be useful to add a peptide to the N-terminal part of the protein, e.g. for purification reasons. It might not be necessary to cleave off this added peptide after expression and purification of the protein. Additional peptides at the N- or C-terminal part of the protein may also serve for the targeting of the protein to special tissues such as nerve or bone tissue or for the penetration of the blood/brain barrier.

Also more preferably, the morphogenetic protein or biologically active part or variant thereof is a protein belonging to the TGF-β, BMP-, GDF-, activin- or GDNF-families but lacking a cysteine residue which is responsible for dimer formation in respective naturally occurring proteins. The protein according to this aspect of the present invention cannot form the disulfide bridge which is present in the wildtype form of the protein. As described in WOO/1041, substitution or deletion of the cysteine, which normally effects the dimerization in the proteins, results upon expression and correct folding (proper formation of the intramolecular disulfide bridges) in a monomeric protein that retains the biological activity of the dimeric form. Generally, also fusion proteins of a monomeric protein according to this aspect of the invention and another peptide or group are considered within the scope of the present invention, wherein these other peptides or groups are directing the localization of the fusion protein, e.g. because of an affinity to a certain tissue type etc. Examples for such fusion proteins are described in WO 97/23612. The protein containing such addition will retain its biological activity at least as long as such addition does not impair the formation of the biologically active conformation of the protein.

Although the biological activities of monomeric and (wild-type) dimeric proteins are comparable, dimeric proteins often exhibit some deviating chemical and biophysical properties. Because of their doubled molecular weight as well as the persisting covalent linkage and intermolecular forces between the two monomeric subunits, dimers expose more and also some different amino acid residues to the surrounding medium than their monomeric equivalents. Dimers consist of two covalently connected subunits which are under all physiological circumstances in close distance to each other, therefore creating multiple types of reciprocal interactions with themselves as well as with the solvent. It is disclosed in the state of the art which amino acid is responsible in a certain protein family or protein for dimer formation (see for example: Schlunegger & Grutter (1992) Nature 358, 430-434; Daopin et al., (1992) Science 257, 369-373 and Griffith et al., Proc. Natl. Acad. Sci. 93 (1996), page 878-883). Especially the amino acids in dose distance to this linkage point between the subunits are never in direct contact with the solvent. Monomers, on the other hand, are usually surrounded entirely by the fluid and don't interact permanently with other monomeric molecules. These differences between monomeric and dimeric morphogenetic proteins are theoretically expected to result in an altered pH-dependent solubility of the monomeric molecules. One further indication towards an altered solubility is given by the experimental determination of the isoelectric point (pI) of both proteins. The isoelectric point is defined as pH at which the net charge of proteins at their pI is zero and the solubility of proteins at the pI reaches a minimum. As it is shown in example 1 and FIG. 1, the pI of the monomeric proteins according to this invention has been determined and it differs clearly from the pI of the dimeric proteins.

In view of this both theoretically and experimentally based prediction of altered solubilities of the monomeric morphogenetic proteins it has been absolutely unexpected that the pH-dependent solubility of the monomeric morphogenetic proteins is nevertheless equivalent to that of their dimeric equivalents.

The present invention is based on the further surprising results that also these monomeric proteins maintain their biological activity at extreme pH values and can be adsorbed on matrix materials without adverse effect on activity and efficiency. It was discovered during the work leading to the present invention that by providing certain pH conditions it is possible to keep monomeric proteins in solution even in presence of matrix materials. Under such conditions the soluble protein can uniformly adsorb to all surfaces attainable to the dissolved protein. The availability of inner surfaces of more or less porous materials will depend on the pore size. Using the conditions described in the present invention it will be possible to adsorb protein on all surfaces which are available to the solubilized protein due to its molecule size. The present invention avoids formation of precipitates and blockage of pores to further access of protein solution. This procedure achieves optimal coating of all available surfaces of the matrix material and the osteoinductive materials of the present invention show improved efficacy as compared to materials of the prior art.

As described in the above mentioned patent application WO01/11041, it was found that at least some of these monomeric proteins show a comparable or even higher activity, based on the weight of protein than their respective dimeric forms. A further important advantage lies in the fact that the proteins can be expressed in a large amount in prokaryotic hosts and upon simple refolding of the monomers they are obtained in high purity and very high yield without the need to separate dimerized from non dimerized (monomeric) proteins. It is preferred that proteins according to this aspect of the invention contain at least the 7 cysteine region characteristic for the TGF-β protein superfamily. It is disclosed in the state of the art which cysteine is responsible in a certain protein family or protein for dimer formation (see for example: Schlunegger & Grutter (1992) Nature 358, 430-434; Daopin et al., (1992) Science 257, 369-373 and Griffith et al, Proc. Natl. Acad. Sci. 93 (1996), page 878-883). This cysteine has to be deleted or substituted by another amino acid to form a protein used within the framework of this aspect of the present invention.

In an especially preferred embodiment of this aspect of the present invention the protein lacking a cysteine residue which is responsible for dimer formation contains a consensus sequence according to the following sequence $$CC(Y)_{25\text{-}29}CYYYC(Y)_{25\text{-}35}XC(Y)_{27\text{-}34}CYC \qquad \text{(Formula I)},$$

wherein C denotes cysteine, Y denotes any amino acid including cysteine and X denotes any amino acid except cysteine.

More preferably the protein lacking a cysteine residue which is responsible for dimer formation according to this aspect of the invention contains a consensus sequence according to the following sequence $$C(Y)_{28}CYYYC(Y)_{30\text{-}32}XC(Y)_{31}CYC \qquad \text{(Formula II)},$$

wherein C, X and Y have the same meaning as defined above.

Even more preferably the protein lacking a cysteine residue which is responsible for dimer formation according to this aspect of the invention contains a consensus sequence according to the following sequence $$C(X)_{28}CXXXC(X)_{31\text{-}33}C(X)_{31}CXC \qquad \text{(Formula III)},$$

wherein C and X have the same meaning as defined above.

In these consensus sequences especially preferred distances between the respective cysteine residues are contained, wherein also already the dimer forming cysteine is substituted by another amino acid. As with all proteins of said protein superfamily the location of and distance between the cysteines is more important than the identity of the other amino acids contained in this region. Therefore, the consensus sequence shows the respective location of the cysteines, but does not show the identity of the other amino acids, since these other amino acids are widely variable in the proteins of the TGF-β protein superfamily.

In an especially preferred embodiment the protein contained in the osteoinductive material is a monomeric form of MP52 and comprises at least the mature part of the amino acid sequence according to SEQ.ID.NO.1 (DNA and protein sequence) and SEQ.ID.NO.2 (protein sequence, only), wherein the amino acid indicated by Xaa at pos. 465 is either deleted or any amino acid except cysteine. Especially other hydrophobic amino acids such as glycine, valine, leucine or isoleucine can be present at pos. 465. The start of the mature protein lies preferably in the area of amino acids 352-400, especially preferred at amino acids 381 or 382. Therefore, the mature protein comprises amino acids 381-501 or 382-501. The first alanine of the mature protein can be deleted and the mature protein then preferably comprises amino acids 383-501.

The most preferred protein used within the present invention is MP52-Ala83, a protein starting at amino acid 383 of SEQ.ID.NO.1 or 2, wherein the naturally occurring cysteine at position 465 is replaced by the hydrophobic amino acid alanine. Also for MP52-Ala83, the mature protein starts preferably between amino acids 352-400, especially preferred at amino acids 381 or 382. The first alanine of the mature protein can be deleted and the mature protein then preferably comprises amino acids 383-501.

It is theoretically possible that proteins which correspond to the definition of monomeric proteins as used in this context, form some kind of aggregates in solution. However, this aggregates do not correspond to dimers or multimers of proteins formed by defined intermolecular bridges and covalent binding. Nevertheless, van der Waals forces and other forms of weak binding can occur and such aggregates are considered to be encompassed by the present invention.

Another aspect of the present invention is a process for the production of an osteoinductive material of the invention. Said process comprises contacting a matrix material with a solution of morphogenetic protein(s) under suitable conditions to keep the protein stable and dissolved in a buffered solution and thereby allowing that the matrix material becomes evenly coated with the morphogenetic proteins and subsequently drying of the coated matrix material. The process provides for selecting and adjusting the pH of the protein solution to a value of 5.2 or lower or 9.5 and higher, also when in contact with the matrix material. Preferred are pH values between 12 and 13. Especially preferred are pH values between 2 and 4.5, between 4.5 and 5.2, between 9.5 and 10.3 and between 10.3 and 12. Proteins and matrix materials that can form the osteoinductive materials are as described above for the other subjects of the present invention, also all suitable solvents/buffers, additives and auxiliaries.

The following nonlimiting examples together with the figures and sequence protocols are intended to further illustrate the invention.

SEQ.ID.NO.1 shows the DNA and protein sequence and SEQ.ID.NO.2 the protein sequence of MP52 and MP52-Ala83 prepro-peptides, wherein the amino acid indicated by Xaa at pos. 465 is either cysteine (in case of MP52) or alanine (in case of MP52-Ala83). The naturally occurring mature proteins MP52 and MP52-Ala83 comprise amino acids 382-501. In preferred recombinant variants of MP52 and MP52-Ala83, the first alanine of the mature protein is deleted and the mature protein comprises amino acids 383-501. In all following figures and examples, this recombinant versions of MP52 and MP52-Ala83 have been used.

FIG. 1 shows the results of the isoelectric focusing according to example 1. MP52-Ala83 is present in lane 1, whereas MP52 is present in lane 2. The pI of MP52 is approximately 7.65 and the pI of MP52-Ala83 is approximately 7.1.

Figure 2:
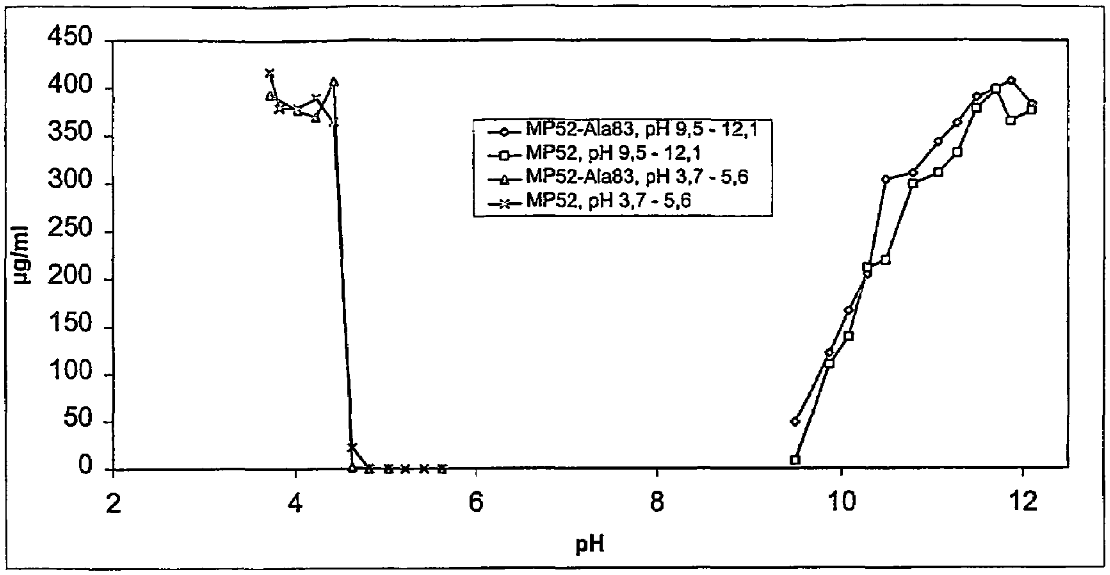

FIG. 2 shows a comparison of the pH-dependent solubility of MP52 and MP52-Ala83 according to examples 2 and 3 and to the table below. The buffers (0.1 M sodium acetate-acetic acid (p. 429) and 0.1 M sodium carbonate-sodium bicarbonate (p. 439) were prepared according to Dawson et al.: Data for biochemical research (Third edition) 1986, p. 429 and p. 439, Clarendon Press, Oxford. Thus, concerning the pH-dependent solubility it can be stated that MP52 and MP52-Ala83 exhibit nearly identical properties.

| SAMPLE | pH | SOLVENT | RECOVERY (%) | RECOVERY (μg/ml) |
|---|---|---|---|---|
| MP52-Ala83 | 9.50 | Sodium carbonate 0.1 M | 12.2 | 48.96 |
| MP52-Ala83 | 9.87 | Sodium carbonate 0.1 M | 30.4 | 121.76 |
| MP52-Ala83 | 10.08 | Sodium carbonate 0.1 M | 41.5 | 166.16 |
| MP52-Ala83 | 10.29 | Sodium carbonate 0.1 M | 51.2 | 204.64 |
| MP52-Ala83 | 10.49 | Sodium carbonate 0.1 M | 75.8 | 303 |
| MP52-Ala83 | 10.79 | Sodium carbonate 0.1 M | 77.5 | 309.84 |
| MP52-Ala83 | 11.07 | Sodium carbonate 0.1 M | 85.7 | 342.96 |
| MP52-Ala83 | 11.28 | Sodium carbonate 0.1 M | 90.7 | 362.6 |
| MP52-Ala83 | 11.49 | Sodium carbonate 0.1 M | 97.6 | 390.48 |
| MP52-Ala83 | 11.70 | Sodium carbonate 0.1 M | 99.8 | 399.04 |
| MP52-Ala83 | 11.87 | Sodium carbonate 0.1 M | 101.7 | 406.96 |
| MP52-Ala83 | 12.10 | Sodium carbonate 0.1 M | 95.8 | 383.36 |
| MP52 | 9.50 | Sodium carbonate 0.1 M | 2.1 | 8.32 |
| MP52 | 9.87 | Sodium carbonate 0.1 M | 27.5 | 110.16 |
| MP52 | 10.08 | Sodium carbonate 0.1 M | 34.7 | 138.8 |
| MP52 | 10.29 | Sodium carbonate 0.1 M | 52.8 | 211.2 |
| MP52 | 10.49 | Sodium carbonate 0.1 M | 54.8 | 219.12 |
| MP52 | 10.79 | Sodium carbonate 0.1 M | 74.6 | 298.32 |
| MP52 | 11.07 | Sodium carbonate 0.1 M | 77.6 | 310.32 |
| MP52 | 11.28 | Sodium carbonate 0.1 M | 82.9 | 331.4 |

-continued

| SAMPLE | pH | SOLVENT | RE-COVERY (%) | RE-COVERY (µg/ml) |
|---|---|---|---|---|
| MP52 | 11.49 | Sodium carbonate 0.1 M | 94.6 | 378.56 |
| MP52 | 11.70 | Sodium carbonate 0.1 M | 99.5 | 398.16 |
| MP52 | 11.87 | Sodium carbonate 0.1 M | 91.2 | 364.8 |
| MP52 | 12.10 | Sodium carbonate 0.1 M | 94.1 | 376.52 |
| MP52-Ala83 | 3.72 | Sodium acetate 0.1 M | 98.4 | 393.48 |
| MP52-Ala83 | 4.03 | Sodium acetate 0.1 M | 94.3 | 377.2 |
| MP52-Ala83 | 4.23 | Sodium acetate 0.1 M | 92.4 | 369.56 |
| MP52-Ala83 | 4.43 | Sodium acetate 0.1 M | 101.9 | 407.48 |
| MP52-Ala83 | 4.63 | Sodium acetate 0.1 M | 0.5 | 1.88 |
| MP52-Ala83 | 4.82 | Sodium acetate 0.1 M | 0.0 | 0 |
| MP52-Ala83 | 5.03 | Sodium acetate 0.1 M | 0.0 | 0 |
| MP52-Ala83 | 5.63 | Sodium acetate 0.1 M | 0.0 | 0 |
| MP52 | 3.72 | Sodium acetate 0.1 M | 104.3 | 417.2 |
| MP52 | 3.83 | Sodium acetate 0.1 M | 94.8 | 379.2 |
| MP52 | 4.03 | Sodium acetate 0.1 M | 94.8 | 379.2 |
| MP52 | 4.23 | Sodium acetate 0.1 M | 97.5 | 390 |
| MP52 | 4.43 | Sodium acetate 0.1 M | 91.2 | 364.8 |
| MP52 | 4.63 | Sodium acetate 0.1 M | 5.6 | 22.4 |
| MP52 | 4.82 | Sodium acetate 0.1 M | 0.1 | 0.4 |
| MP52 | 5.03 | Sodium acetate 0.1 M | 0.0 | 0 |
| MP52 | 5.22 | Sodium acetate 0.1 M | 0.0 | 0 |
| MP52 | 5.43 | Sodium acetate 0.1 M | 0.0 | 0 |
| MP52 | 5.63 | Sodium acetate 0.1 M | 0.0 | 0 |

Figure 3:
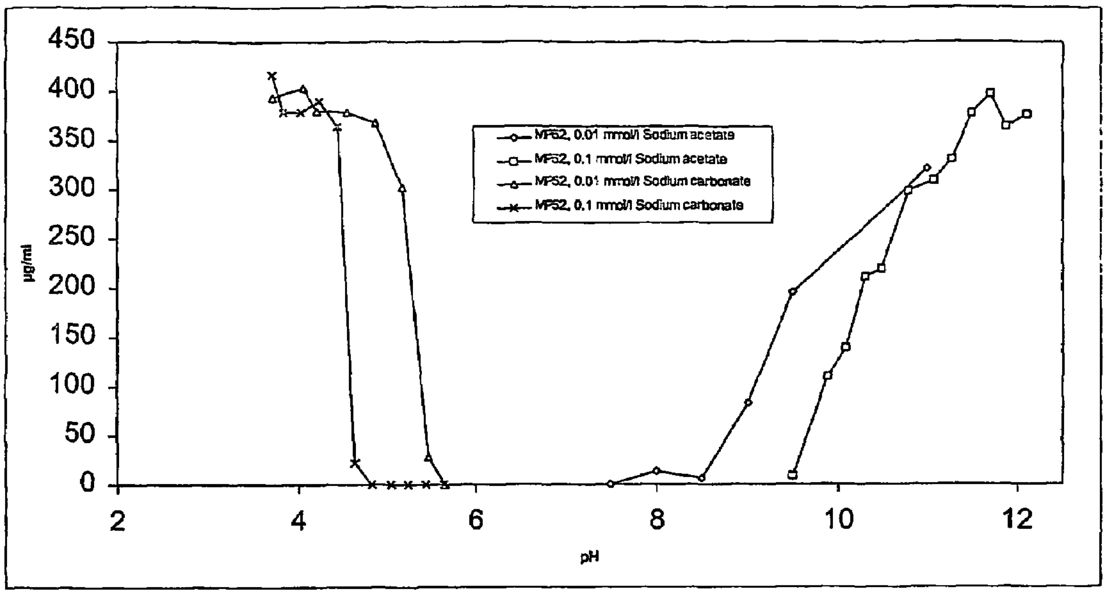

FIG. 3 shows a comparison of the solubility of MP52 in dependence from the ionic strength of the solvent according to examples 2 and 3 and to the table below. The buffers (sodium acetate-acetic acid and sodium carbonate-sodium bicarbonate were prepared according to Dawson et al.: Data for biochemical research (Third edition) 1986, p. 429 and p. 439, Clarendon Press, Oxford. In solvents with high ionic strength (0.1 M, see also table corresponding to FIG. 2), protein solubilities of 200 µg/ml or more are achievable at pH values below 4.5 and above 10.3. In solvents with lower ionic strength (0.01 M, see also table below), protein solubilities of about 200 µm/ml or more are achievable at pH values below 5.2 and above 9.5.

| SAMPLE | pH | SOLVENT | RE-COVERY (%) | RE-COVERY (µg/ml) |
|---|---|---|---|---|
| MP52 | 7.50 | 0.01 M Sodium carbonate | 0.0 | 0.08 |
| MP52 | 8.00 | 0.01 M Sodium carbonate | 3.5 | 14 |
| MP52 | 8.50 | 0.01 M Sodium carbonate | 1.6 | 6.32 |
| MP52 | 9.00 | 0.01 M Sodium carbonate | 20.7 | 82.76 |
| MP52 | 9.50 | 0.01 M Sodium carbonate | 48.7 | 194.6 |
| MP52 | 11.00 | 0.01 M Sodium carbonate | 80.5 | 322.16 |
| MP52 | 3.72 | 0.01 M Sodium acetate | 98.4 | 393.48 |
| MP52 | 4.05 | 0.01 M Sodium acetate | 100.9 | 403.56 |
| MP52 | 4.20 | 0.01 M Sodium acetate | 95.1 | 380.28 |
| MP52 | 4.55 | 0.01 M Sodium acetate | 94.8 | 379.2 |
| MP52 | 4.85 | 0.01 M Sodium acetate | 92.0 | 367.92 |
| MP52 | 5.15 | 0.01 M Sodium acetate | 75.5 | 302.16 |
| MP52 | 5.45 | 0.01 M Sodium acetate | 6.9 | 27.56 |
| MP52 | 5.65 | 0.01 M Sodium acetate | 0.1 | 0.52 |

Figure 4:
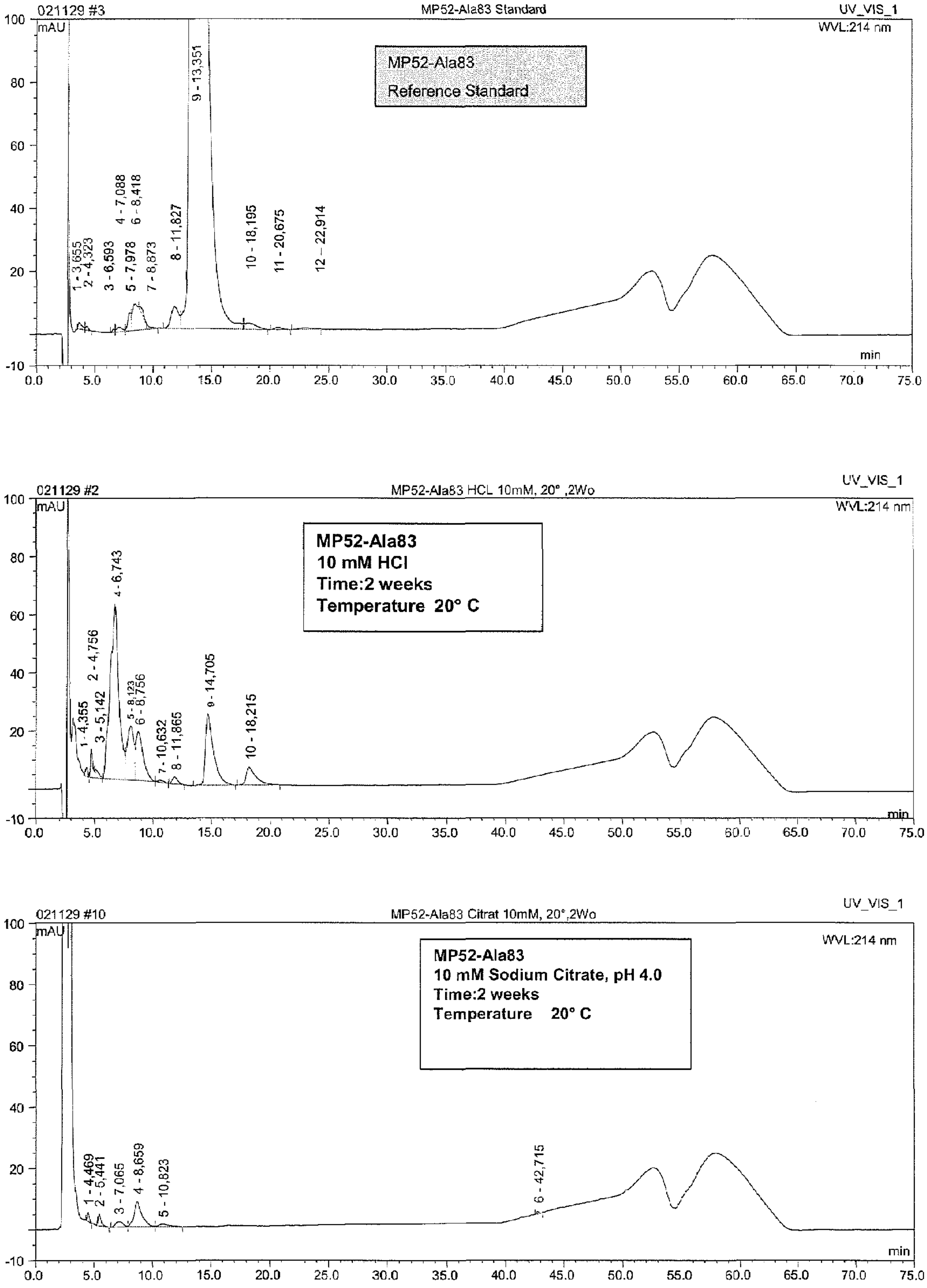
Figure 4:
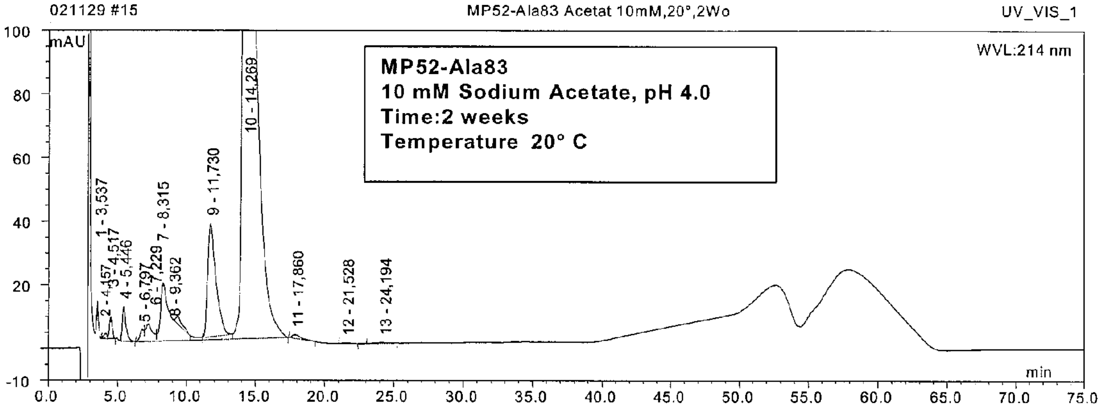
Figure 4:
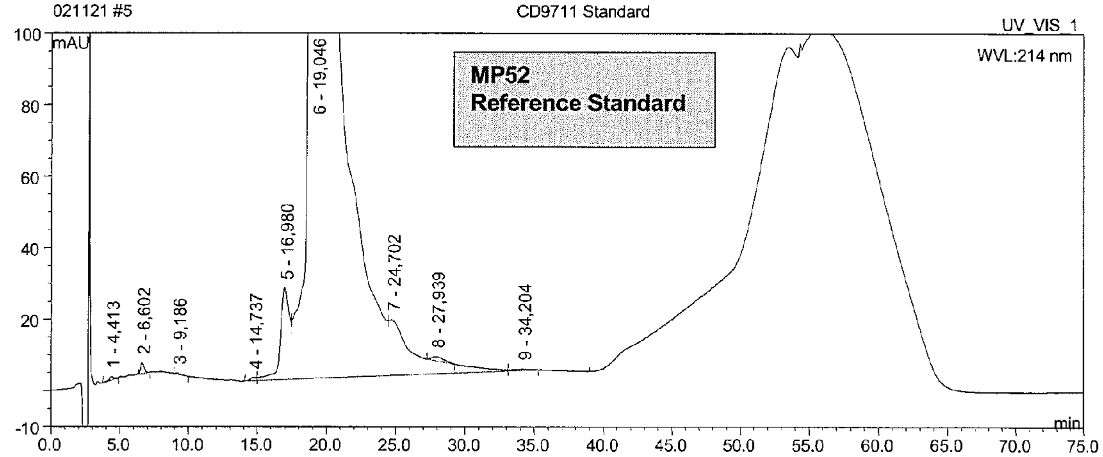
Figure 4:
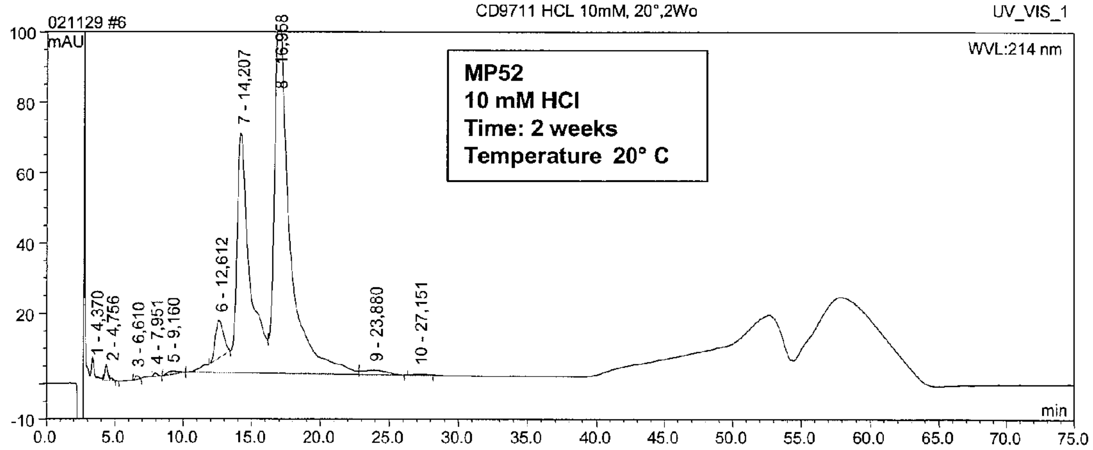
Figure 4:
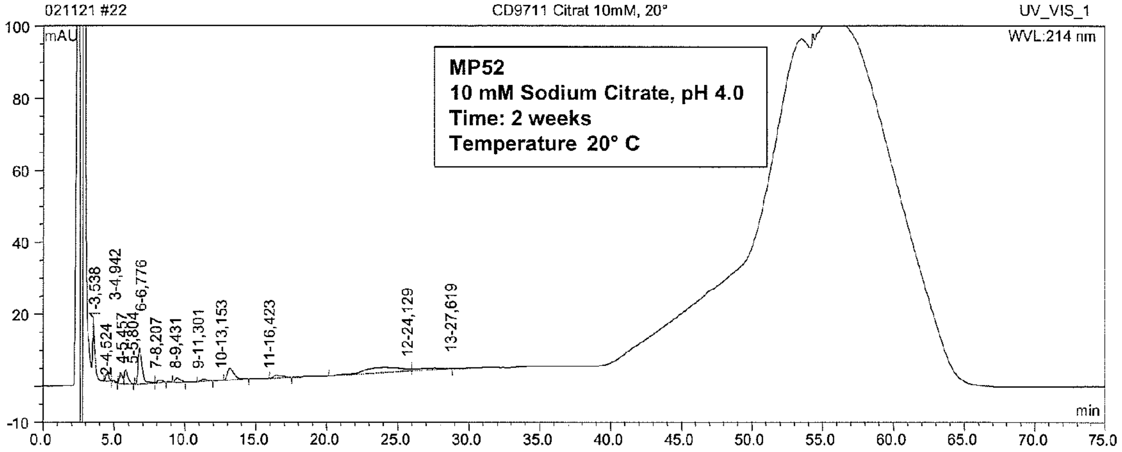
Figure 4:
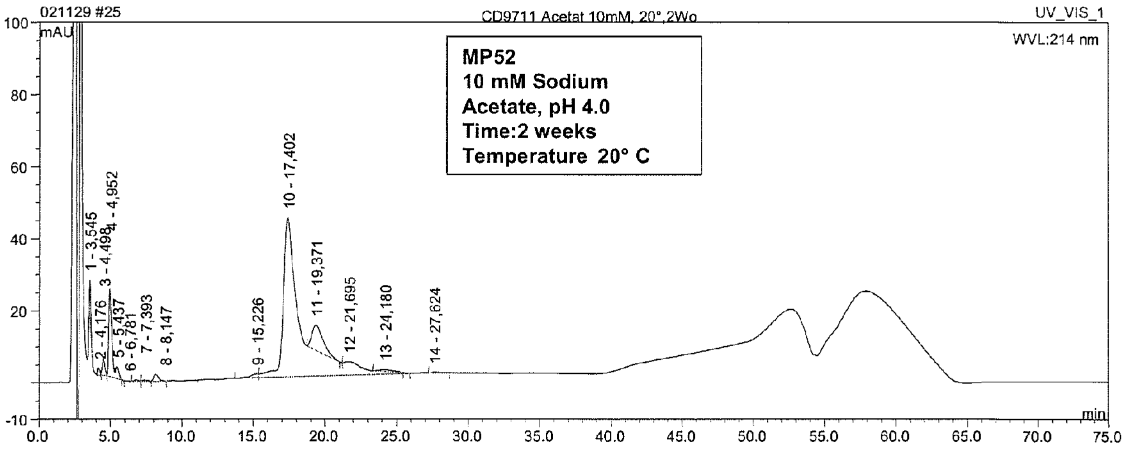

FIG. 4 shows, according to examples 3 and 5, the stability of MP52 and MP52-Ala83 in different buffers (10 mM HCl, 10 mM sodium acetate pH 4.0 and 10 mM sodium citrate pH 4.0) after two weeks of storage at 20° C. as determined by RP-HPLC analysis. The high main peaks representing MP52 (or MP52-Ala83, respectively) are present at about 17-23 min (MP52) and at about 11-18 min (MP52-Ala83). Additional Peaks (Forepeaks) appearing in front of the main peak and in deviation to the untreated Reference Standards indicate degradation products of the proteins. Significant protein degradation appears in 10 mM sodium citrate, whereas the protein stability is improved in 10 mM HCl and especially in 10 mM sodium acetate buffer.

Figure 5:
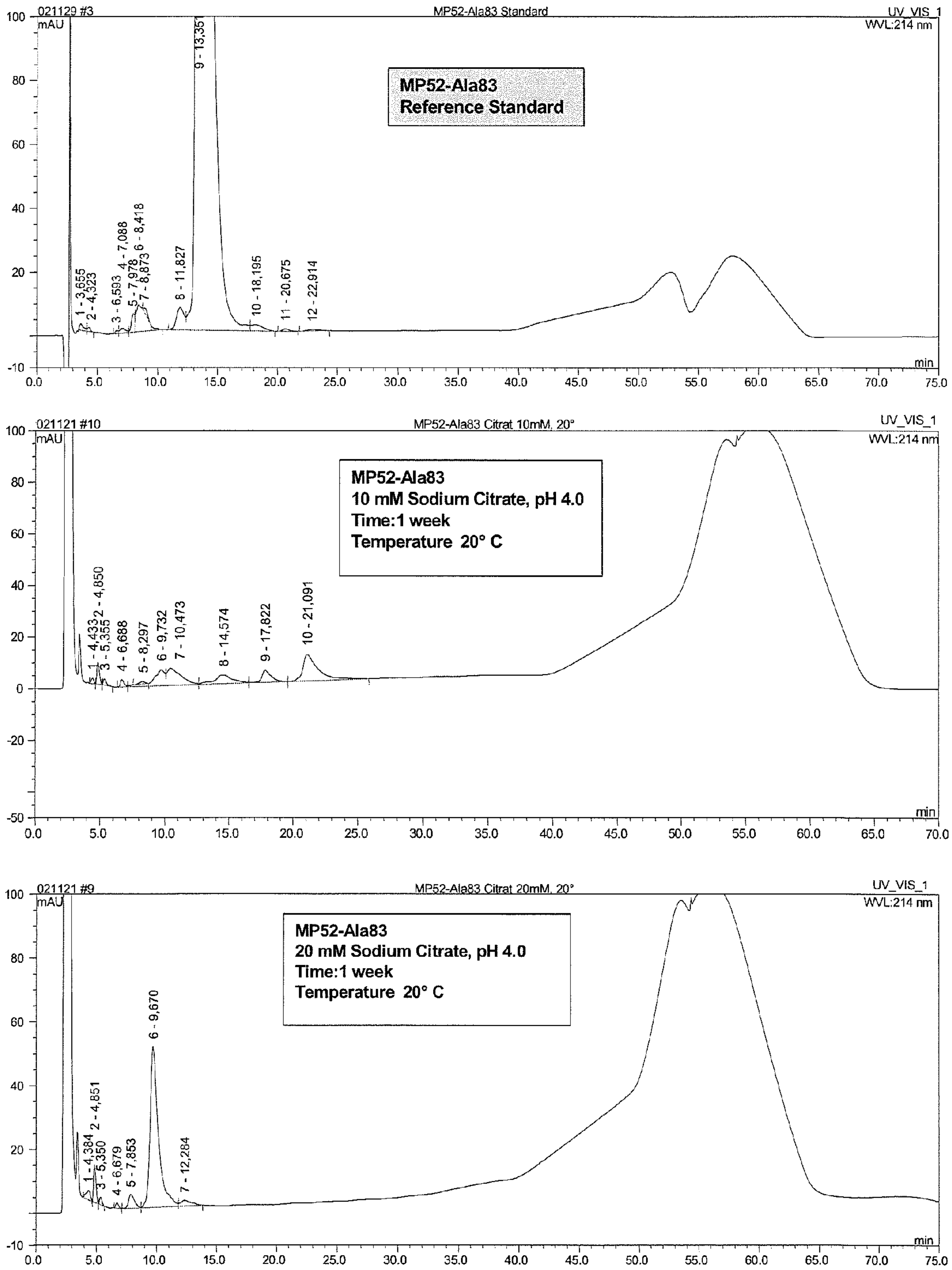
Figure 5:
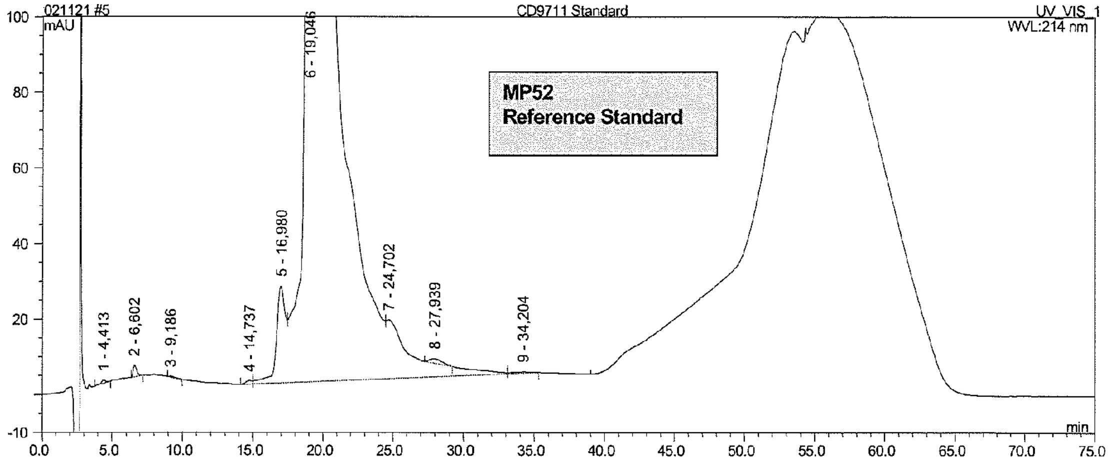
Figure 5:
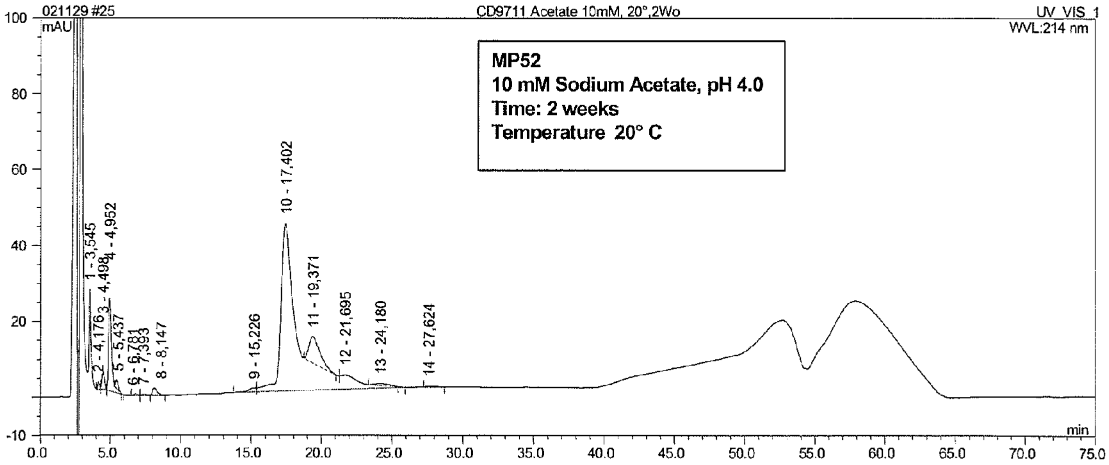
Figure 5:
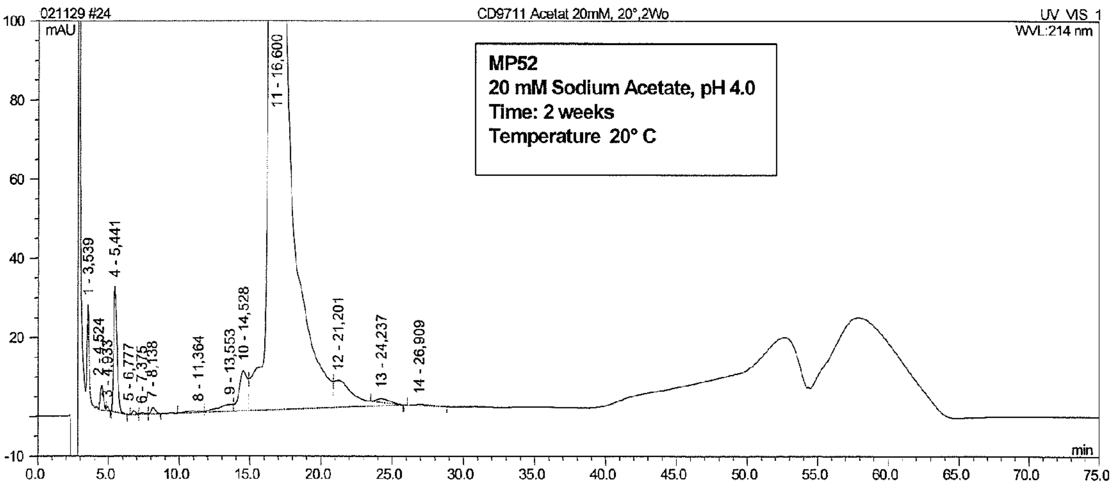

FIG. 5 shows, according to examples 3 and 6, the stability of MP52 and MP52-Ala83 in dependency from the ionic strength of the used buffer/solvent as determined by RP-HPLC analysis. The degradion of MP52 in 10 mM and 20 mM sodium acetate pH 4.0 after two weeks of storage at 20° C. as well as the degradation of MP52-Ala83 in 10 mM and 20 Sodium citrate pH 4.0 after one week of storage at 20° C. are shown as nonlimiting examples. The high main peak representing MP52 (or MP52-Ala83, respectively) is present at about 15-20 min. Additional Peaks (Forepeaks) appearing in front of the main peak and in deviation to the untreated Reference Standards indicate degradation products of the proteins. The protein stability is good in 10 mM sodium acetate but is even better if the proteins are stored in a buffer with moderate ionic strength (20 mM sodium acetate). Even in buffers which are generally not suited for storage of the morphogenetic proteins (sodium citrate), an enhancement of the protein stability is achievable in the buffer with moderate (20 mM) ionic strength.

Figure 6:
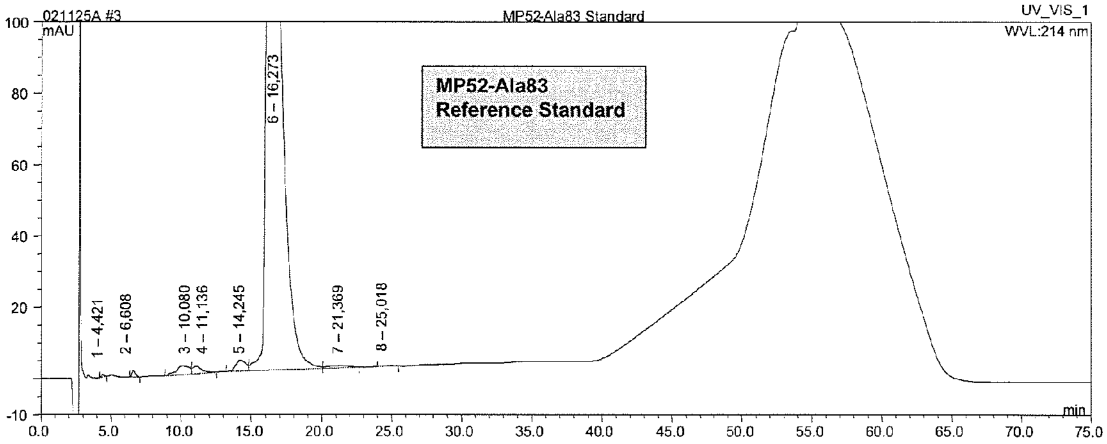
Figure 6:
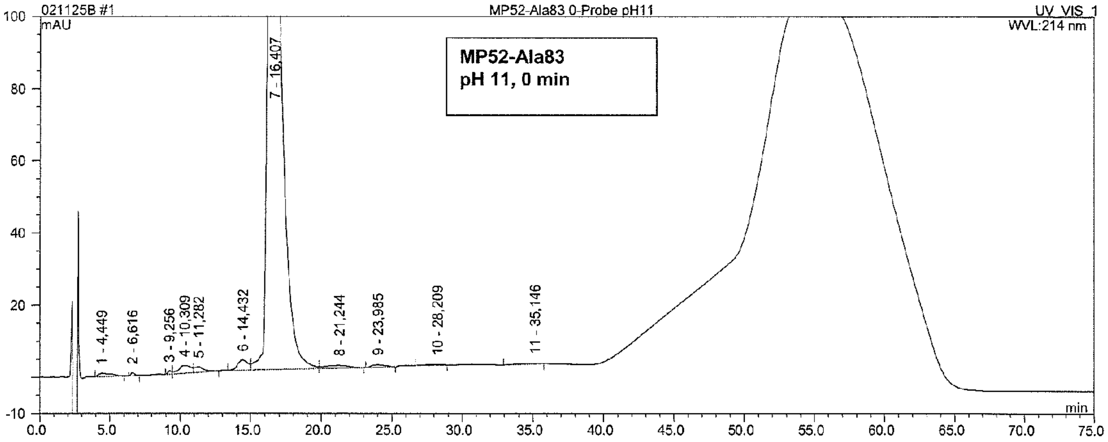
Figure 6:
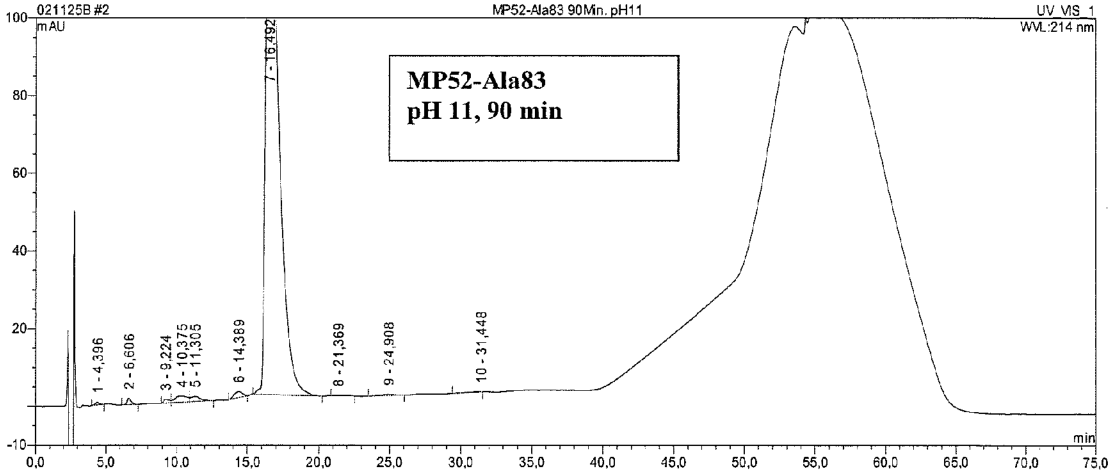
Figure 6:
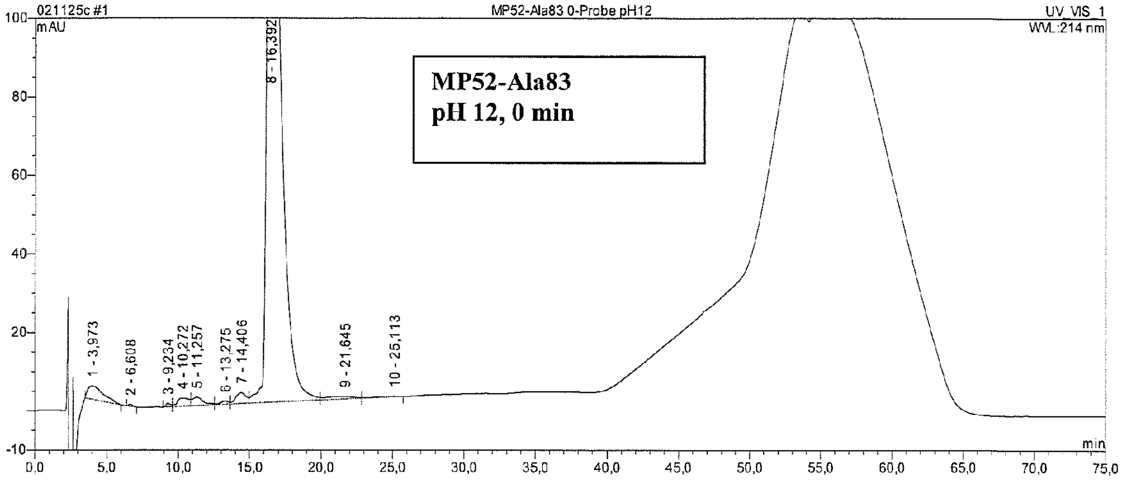
Figure 6:
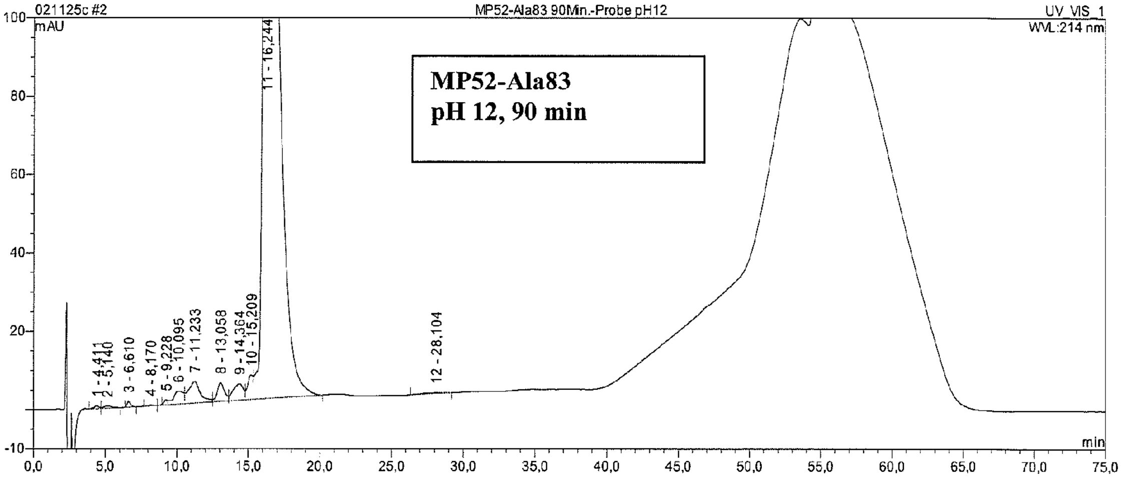
Figure 6:
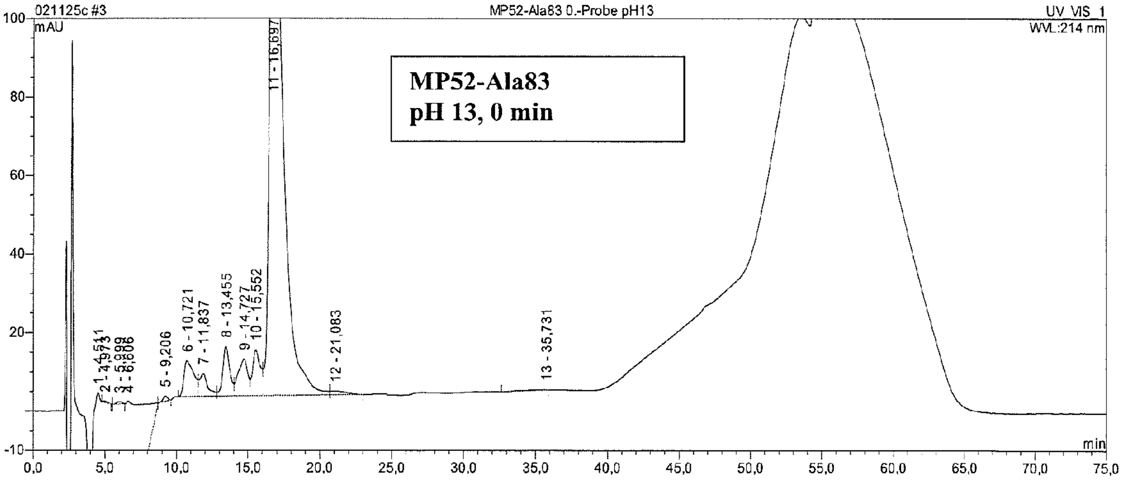
Figure 6:
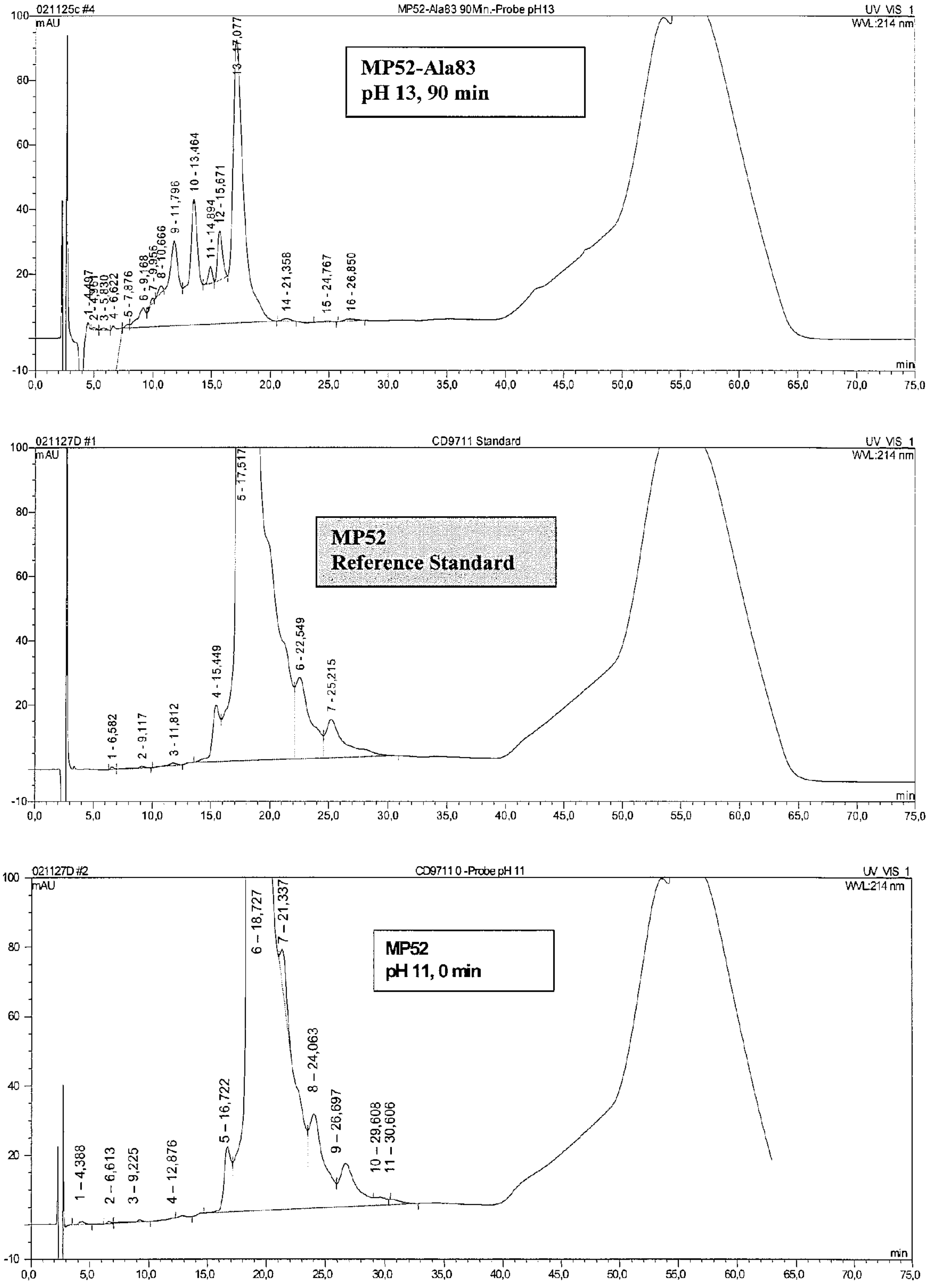
Figure 6:
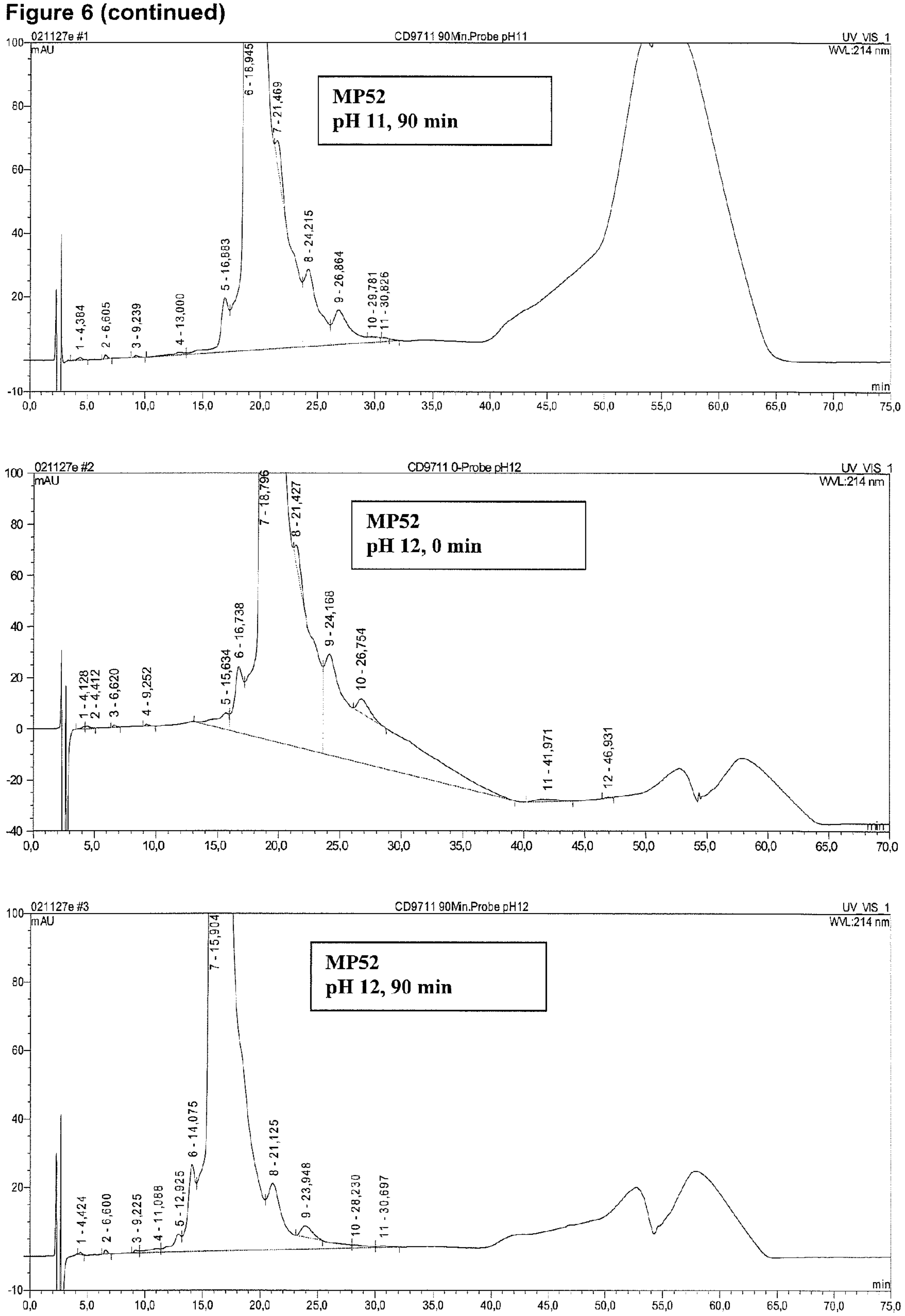
Figure 6:
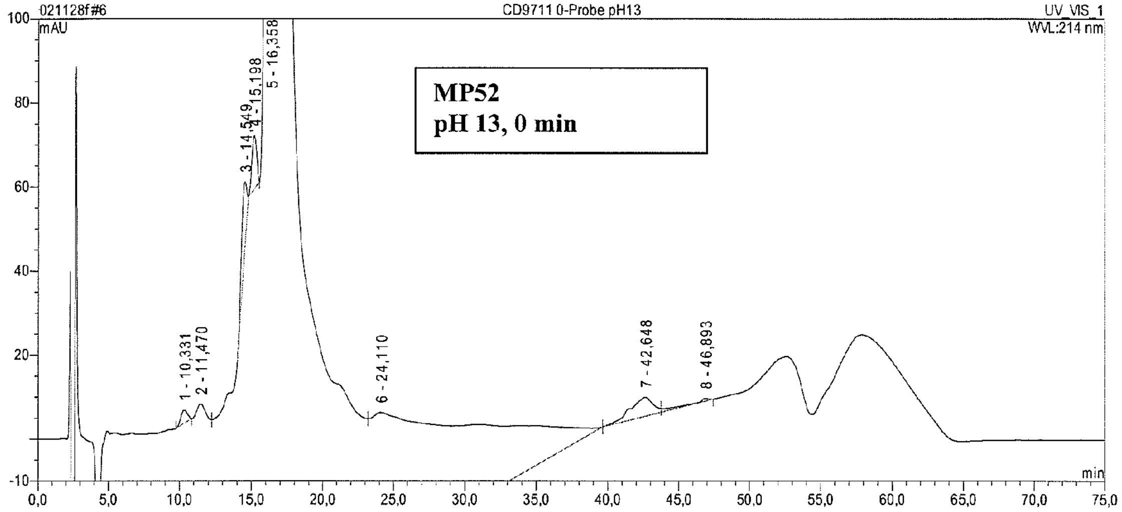
Figure 6:
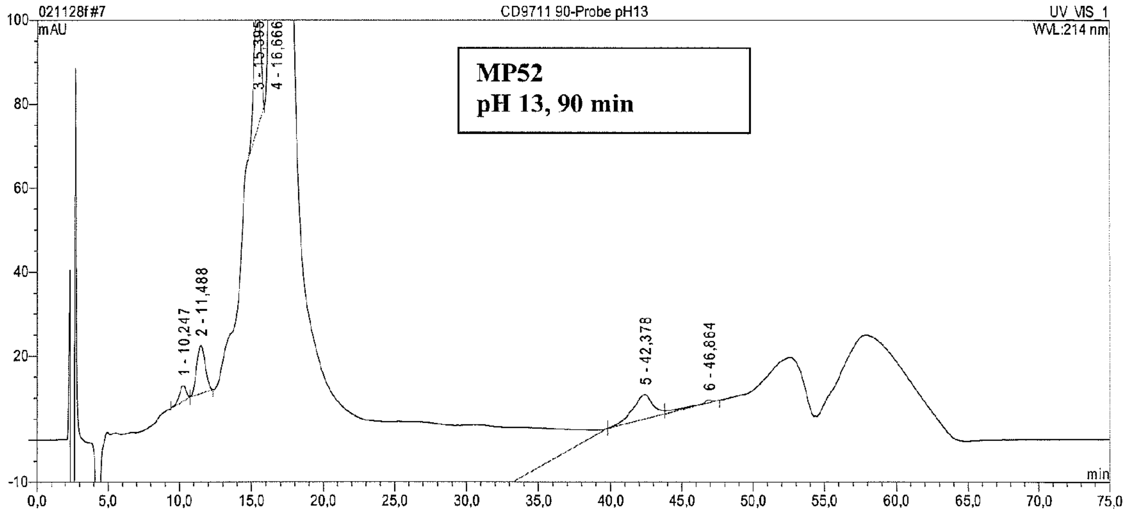

FIG. 6 shows, according to examples 3 and 7, the stability of MP52 and MP52-Ala83 at pH11, pH12 and pH13 after 0 and 90 min as determined by RP-HPLC analysis. The high main peak representing MP52 (or MP52-Ala83, respectively) is present at about 15-20 min. Additional Peals (Forepeaks) appearing in front of the main peak and in deviation to the untreated Reference Standards indicate degradation products of the proteins. The proteins are stable at high pH values at least up to pH12, for shorter periods not exceeding 90 min also at pH13.

Figure 7:
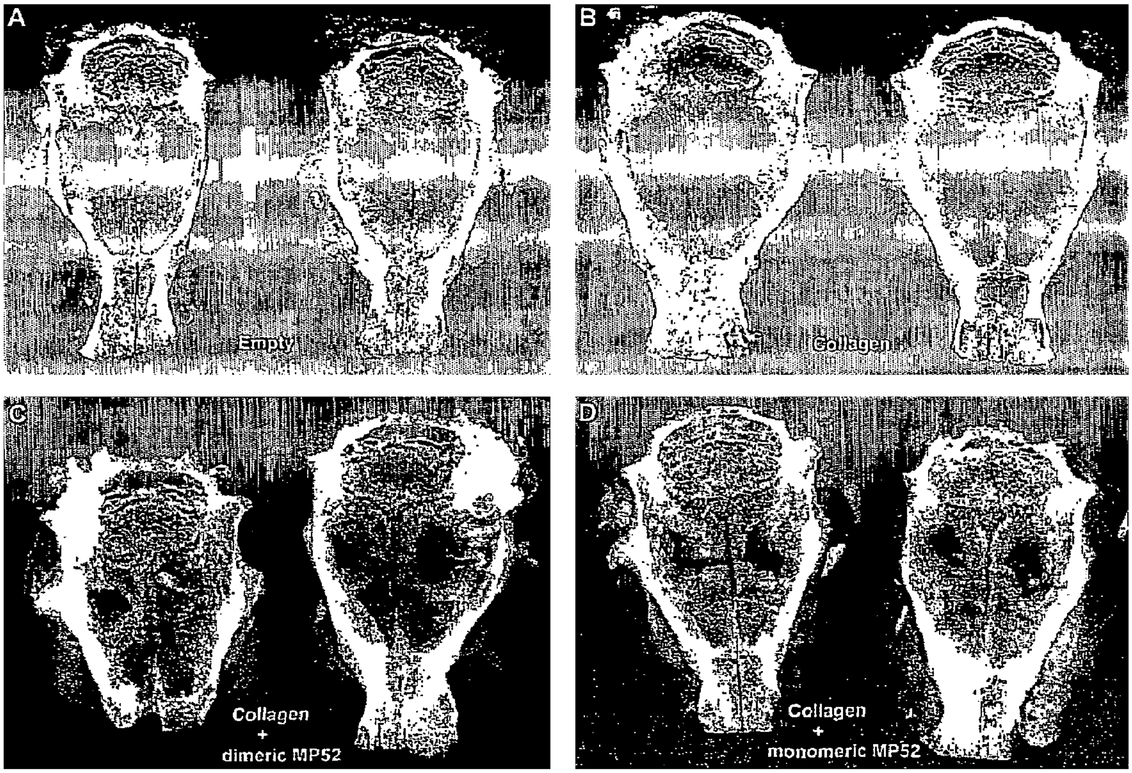

FIG. 7 shows radiographs of rat cranial defects filled with osteoinductive materials 8 weeks post operation according to example 9. A: untreated defects, B: defects treated with collagen sponges alone; C: defects filled with collagen+dimeric MP52; D: defects filled with collagen+monomeric MP52 (MP52-Ala83). Whereas no bone regeneration is visible in untreated (7 A) or solely matrix treated (7B) defects, osteoregeneration is noticeable in cranial defects filled with collagen and morphogenetic protein (7C and 7D).

EXAMPLES

Example 1

Isoelectric Focusing

Isoelectric Focusing was performed under non reducing conditions by using a "CleanGel IEF" gel (Pharmacia, Cat. No. 18-1035-32). Prior to use, the dried gel was rehydrated for 8 hours in a 40 ml aqueous solution containing 19.2 g Urea, 400 µl NP-40 (10% solution), 100 µl Ampholine pH 3.5-10.0 (Pharmacia, Cat. No. 80-1125-87) and 2.5 ml Ampholine pH 7.0-9.0 (Pharmacia, Cat. No. 80-1125-94). The running conditions were as follows:

| Phase | Voltage (V) | Current (mA) | Power (W) | Time (min) |
|---|---|---|---|---|
| Prefocusing | 700 | 12 | 8 | 20 |
| Sample entrance | 500 | 8 | 8 | 60 |
| Isoelectric focusing | 2000 | 14 | 14 | 150 |
| Band sharpening | 2500 | 14 | 18 | 10 |

500 ng protein were applied per lane. After running, the gel was placed 2 times for 15 min each in fixing solution (115 g/l Trichloroacetic Acid and 35 g/l 5-Sulfosalicylic Acid Dihydrate), washed in distilled water and silver stained (see FIG. 1). For determination of pI, after IEF one gel was separately cut from the anode side into 1 cm pieces, which were soaked in water for injection for extraction. When the pH's of the extracts were plotted versus the distance from the anode side, a linearity in the pH gradient was observed over the range of 2.5-7.5 cm from the anode side. The pI values were the determined by measuring the distance between anode (pH 7) and the main band and using linear coherency of pI and distance between anode and main bands. The distance to the anode for the MP52 dimer band was x=5.5 cm and for the MP52-Ala83 band the distance was x=3.2 cm. The used linear equation is $y=0.217*x+6.416$. Therefore, the experimentally determined pI of the MP52 dimer is approximately 7.65 and the pI of MP52-Ala83 is approximately 7.1.

Example 2

Determination of the Protein Solubility

MP52 and/or MP52-Ala83, previously dissolved in 10 mmol/l HCl, were lyophilized. Lyophilisates were dissolved for equal time periods of 5 min in different solvents (see FIGS. 2 and 3) in order to create final protein concentrations of 0.4 mg/ml. Samples were subsequently analysed by RP-HPLC and the recovery rate/amount of dissolved protein was calculated.

Example 3

Reversed Phase HPLC Analysis of Protein Samples

For determination of protein degradation, commonly known Reversed Phase HPLC analysis (RP-HPLC) of samples was performed. RP-HPLC devices of different manufacturers were used. A suitable example for adequate running conditions is: Column: Vydac C18; 5 μm; 300 Angstrom; 2.1×250 mm; Phase 218TP52; Phase A: 0.15% TFA in water; Phase B 0.15% Acetonitril/TFA; Rate: 0.3 ml/min.

Example 4

Influence of Different Solvents on the Solubility of the Proteins

MP52, previously dissolved in 10 mmol/l HCl, was lyophilized. Lyophilisates were dissolved for equal time periods of 5 min in the different solvents in order to create final protein concentrations of 0.4 mg/ml. The solubility was compared by using two fixed pH values (pH 10 and pH 4.6, respectively) lying at the border of pH-dependent solubility. Samples were subsequently analysed by RP-HPLC and the recovery rate/amount of dissolved protein was calculated.

According to the table below, no solubility was measured at pH 10, if AMP (2-Amino-2-methyl-1,3-propanediol-HCl; see Dawson et al.: Data for biochemical research (Third edition) 1986, 437, Clarendon Press, Oxford) or sodium glycine were used as solvents. Good solubility was obtained in sodium carbonate buffer or in unbuffered NaOH solution (pH 10). At pH 4.6, sodium acetate proved to be the better solvent in comparison with sodium citrate.

| SAMPLE | pH | SOLVENT | RECOVERY (%) | RECOVERY (μg/ml) |
|---|---|---|---|---|
| MP52 | 10 | Sodium carbonate 0.1 M | 34.7 | 138.3 |
| MP52 | 10 | AMP 0.1 M | 0.1 | 0.4 |
| MP52 | 10 | Sodium glycine 0.1 M | 0.0 | 0.0 |
| MP52 | 10 | NaOH | 97 | 388 |
| MP52 | 4.6 | Sodium acetate 0.1 M | 5.6 | 22.4 |
| MP52 | 4.6 | Sodium citrate 0.1 M | 1.1 | 0.62 |

Example 5

Influence of Different Solvents on Protein Stability

MP52 and MP52-Ala83 were dissolved in three different solvents, one unbuffered solution (10 mM HCl) and two buffered solutions (10 mM sodium acetate pH 4.0, 10 mM sodium citrate pH 4.0). All samples were stored at 20° C. After two weeks, the samples were subjected to Reversed Phase HPLC analysis (Example 3) to determine any degradation of the proteins. The results are shown in FIG. 4. In comparison with a MP52 or MP52-Ala83 reference standard stored at −80° C., the proteins exhibit a significant degradation pattern if solved in 10 mM sodium citrate, whereas much less degradation can be seen in 10 mM HCl. Best results were obtained by storage in 10 mM Sodium acetate buffer.

Example 6

Influence of Buffers Having Different Ionic Strength on Protein Stability

MP52 and MP52-Ala83 were dissolved in 10 or 20 mM sodium acetate, pH 4 or in 10 or 20 mM Sodium citrate, pH 4. All samples were stored at 20° C. After one or two weeks, the samples were subjected to Reversed Phase HPLC analysis (Example 3) to determine any degradation of the proteins. The results are shown in FIG. 5. The protein stability is good in 10 mM sodium acetate but is significantly enhanced if the proteins are stored in a buffer with moderate ionic strength (20 mM sodium acetate). Even in buffers which are generally not suited for storage of the morphogenetic proteins (sodium citrate), an enhancement of the protein stability is achievable in the buffer with the higher ionic strength.

Example 7

Stability of MP52 and MP52-Ala83 at pH 11, pH12, pH13

For stability determination of morphogenetic proteins at basic pH values, MP52 and MP52-Ala83 were dissolved in $Na_2HPO_4$ buffer. The pH was adjusted with NaOH to either pH11, pH12 or pH13. After 0 and 90 min the samples were subjected to Reversed Phase HPLC analysis to determine any degradation of the proteins. As it is shown in FIG. 6, in comparison with a MP52 or MP52-Ala83 reference standard, no major alteration of the peak profile could be seen after 0 and 90 min at pH 11 and pH12, whereas a significant increase of forepeaks representing degradation products is clearly visible after 90 min at pH13. However, a major portion of the MP52 main peak is still present at pH13. Therefore this example proved stability of morphogenetic proteins at high pH values at least up to pH12. Furthermore, these proteins are also stable at pH13 for short periods not exceeding 90 min.

Example 8

Acidic Coating of Matrix Materials for Generating an Even Protein Distribution

This general coating procedure is preferably advantageous for the coating of matrix materials with neutral or basic properties, but can also be used for the coating of acidic carriers.

MP52-Ala83 was dissolved in 10 mM HCl, 10 mM sodium acetate (pH 4) or 20 mM sodium acetate or combinations thereof to give a final concentration of 1 μg/ml. Optionally the solutions contained one or more of the following additives: 8-15% saccharides, 50-60% alcohols, 10-75% syndets. The solutions were subsequently pipetted to a β-TCP matrix material. 100 ng MP52-Ala83 was used for coating of 100 mg matrix material. The coated β-TCP was air dried for 1 hour at 20° C. and finally air-dried or vacuum-dried to remove any remaining fluid.

Example 9

Acidic Coating of a Collagen Carrier and Demonstration of Osteoinduction In Vivo Absorbable hemostatic collagen sponges (type "Helistat", Integra Life Sciences, Plainsboro, USA) were cut in small (0.6 cm×0.6 cm) pieces. Subsequently, the rough sides of the sponges were coated with 60 μl of either dilution buffer alone (10 mM HCl/20 mM sodium acetate, pH 4.0) as a negative control, monomeric MP52-Ala83 (500 μg/ml in dilution buffer) or dimeric MP52 (500 μg/ml in dilution buffer). The sponge matrices were air dried under sterile conditions. The ability of these osteoinductive materials to induce new bone growth in vivo was subsequently evaluated by using a rat cranial defect study. In this well established animal model, circular bone defects are drilled into the cranium of rats and matrix implants coated with morphogenetic proteins are placed within the naturally nonhealing holes. After a couple of weeks, the effectivity of the osteoinductive materials to induce new bone growth can be calculated by determination of defect size reduction.

The sponge collagen matrices were rehydrated prior to implantion in 30 μl phospate buffered saline (PBS) for 10 min. The implants were finally placed into bilateral defects (diameter 6 mm each), which have been created in the parietal bones of rats according to a previously described by Mulliken, J. B. and Glowacki, *J. Plast. Reconstr. Surg.* 65: 553-559 (1980). Implants containing pure collagen without any morphogenetic protein served as negative control, as well as defects without implants. After 8 weeks, animals were sacrified and contact radiographs were taken. The radiographs of the rat cranial defects revealed significant differences (FIG. 7). No bone regeneration could be observed in untreated defects (7 A) or defects treated with collagen sponges alone (7 B). Animals in which the cranial defects had been filled with collagen+dimeric MP52 (7 C) showed strong bone growth starting from the defect borders. Comparable osteoinductive effects were noticeable in specimens treated with collagen+ monomeric MP52 (MP52-Ala83) (7 D).

Example 10

Basic Coating of Matrix Materials for Generating an Even Protein Distribution

This general basic coating procedure is preferably advantageous for the coating of matrix materials with acidic or neutral properties, but can also be used for the coating of basic carriers. Furthermore, MP52 and MP52-Ala83 were dissolved in 10 or 20 mM sodium carbonate/sodium bicarbonate buffer or NaOH (pH 12) to give a final concentration of 1 μg/ml. Optionally the solutions contained one or more of the following additives: 8-15% saccharides, 50-60% alcohols, 10-75% soaps or syndets. The solutions were subsequently pipetted to a β-TCP matrix material. Within this procedure, 100 ng MP52-Ala83 was used for coating of 100 mg matrix material. The coated β-TCP was air dried for 1 hour at 20° C. and finally vacuum-dried to remove any remaining fluid.

Example 11

Coating of a $Ca(OH)_2$ Carrier at pH 12 and Measurement of the Biological Activity In Vivo Conventional $Ca(OH)_2$ powder, which is routinely used as a matrix material in tooth repair procedures, was sterilized for 1 hour at 180° C. prior to the coating. $Ca(OH)_2$ exhibits an strongly basic pH of 12 in aqueous solutions. During the coating procedure, 71 mg sterilized $Ca(OH)_2$ powder was mixed 1:1 with 71 μl solubilized MP52 (3.15 mg/ml) or 71 μl $H_2O$ as a control and incubated to form an osteoinductive material with a pH value of 12.

In order to prove the stability of MP52 at basic pH values, the biological activity of coated MP52 was tested after the coating procedure. The osteoinductive material was neutralized with 1M HCl and subsequently diluted with cell culture medium to release the morphogenetic protein and to produce final protein concentrations of 400 ng/ml and 133.2 ng/ml MP52. The biological activity of these MP52 solutions was measured in vitro by quantification of alkaline phosphatase (ALP) activity using the established mouse cell line MCHT-1/26. The cells were incubated for 3 days in alpha-MEM medium containing 10% FCS, L-Glutamine (20 mM) and penicillin/streptomycin to a confluence of less then 95%. The washed, trypsin treated cells were resuspended in the same culture medium and dispensed in 96-well microtiter plates ($4.5\times10^3$ cells per well). The cells were allowed to adhere for 24 hours, washed (alpha-MEM containing L-Glutamin (20 mM) and subjected to the concentrations of MP52 diluted in culture medium. All values of the MP52 samples were compared to a standard of MP52, for which the in vivo bone formation activity has been determined. The cells were incubated for 72 hours, washed and lysed by incubation in 0.2% Nonidet P-40 detergent and 1 mM $MgCl_2$ over night. The supernatant was mixed with p-nitrophenylphosphate, the substrate for alkaline phosphatase, and the reaction stopped after 1 hour at 37° C. Changes in absorbance at 405 nm were measured and used as indicator of the relative biological activity. The $OD_{405}$ values of MP52 used in the $Ca(OH)_2$ coating procedure (400 ng/ml: 0.629; 133.2 ng/ml: 0.378) are comparable to those of the MP52 standard (400 ng/ml: 0.684; 133.2 ng/ml: 0.438), whereas the control showed no absorbance at 450 nm. Therefore this example proved the possibility to coat matrix materials with morphogenetic proteins at high pH values without loss of biological activity.

Example 12

Coomassie Staining for Detection of the Evenness of the Coating

The amount of protein bound on the matrix material was visualized by Coomassie staining. Coomassie Brilliant Blue is a synthetic heterocyclic organic stain binding nonspecifically but in an approximately stoichometric manner to virtually all proteins. Acidified Coomassie Blue dye changes from reddish-brown to blue when it binds to protein. Thus, an uneven protein distribution on the matrix material is represented by a spotted blue pattern.

Coated matrix materials were incubated with Coomassie staining solution (0.5% Coomassie Brilliant Blue R-250 in 40% methanol, 60% PBS) for 20 min at room temperature. Identical uncoated matrix materials were also stained and served as controls. Any excess of dye was removed by washing with 40% methanol/60% PBS until complete destaining of the controls happened.

An absolutely even protein distribution on the matrix materials without any blue spots was recognized by coating in the presence of polysaccarides, especially sucrose. Similar results were obtained in the presence of alcohols, especially ethanol, soaps or syndets.

---

The invention claimed is:

1. Osteoinductive material comprising a matrix material and, adsorbed on inner and/or outer surfaces of this matrix material, morphogenetic protein(s), wherein said osteoinductive material is obtained by contacting the matrix material and the morphogenetic protein(s) under suitable conditions to keep the protein stable and dissolved in a solution, thereby allowing the matrix material to become evenly coated with the morphogenetic protein(s), wherein said suitable conditions are (a) using a buffer or solvent which is capable of maintaining a pH above 10.3 during the coating procedure, or (b) using a buffer or solvent which has an ionic concentration of 20 mmol/l or less and is capable of maintaining a pH below 5.2 during the coating procedure, or (c) using a buffer or solvent which has an ionic concentration of 100 mmol/l or less and is capable of maintaining a pH above 9.5 during the coating procedure.

2. Osteoinductive material according to claim 1, wherein the morphogenetic protein contains at least a 7 cysteine region characteristic for TGF-β superfamily proteins.

3. Osteoinductive material according to claim 1, wherein the morphogenetic protein is a mature protein or a biologically active part or variant thereof.

4. Osteoinductive material according to claim 1, wherein the morphogenetic protein belongs to the TGF-β-, BMP-, GDF-, activin- or GDNF-family.

5. Osteoinductive material according to claim 1, wherein the morphogenetic protein is a dimeric protein.

6. Osteoinductive material according to claim 1, wherein the morphogenetic protein is BMP2, BMP7, BMP12, BMP13, MP52 (GDF5) or a biologically active part or variant thereof.

7. Osteoinductive material according to claim 1, wherein the morphogenetic protein is a protein lacking the cysteine residue which is responsible for dimer formation in the respective naturally occurring proteins.

8. Osteoinductive material according to claim 1, wherein the morphogenetic protein contains a consensus sequence according to $$C(Y)_{25-29}CYYYC(Y)_{25-35}XC(Y)z,_{27-34}CYC \text{ or} \quad \text{Formula I}$$

$$C(Y)_{28}CYYYC(Y)_{30-32}XC(Y)_{31}CYC, \quad \text{Formula II}$$

wherein C denotes cysteine, Y denotes any amino acid and X denotes any amino acid except cysteine.

9. Osteoinductive material according to claim 1, wherein the protein is a monomeric form of MP52.

10. Osteoinductive material according to claim 9, wherein the protein is MP52-Ala83 or a biologically active part or variant thereof.

11. Osteoinductive material according to claim 1, wherein the matrix material is a biocompatible material.

12. Osteoinductive material according to claim 1, wherein the matrix material is a natural material, a modified natural material or a synthetic material.

13. Osteoinductive material according to claim 1, wherein the matrix material is a porous material.

14. Osteoinductive material according to claim 1, wherein the matrix material comprises at least one of the following substances: a) collagen, b) $Ca(OH)_2$, c) polylactide or polylactide derivatives, d) hyaluronic acid, e) polyoxyethylene polyoxypropylene copolymers f) calcium phosphate, g) a combination of hydroxy apatite and collagen h) a combination of polyglycolic acid and polylactic acid or polylactid derivatives.

15. Osteoinductive material according to claim 1, wherein the buffer or solvent used for coating has an ionic concentration of 20 mmol/l or less.

16. Osteoinductive material according to claim 1, wherein the buffer or solvent used for coating further comprises saccharides.

17. Osteoinductive material according to claim 1, wherein the buffer or solvent used for coating further comprises alcohols or other organic solvents.

18. Osteoinductive material according to claim 1, wherein the buffer or solvent used for coating further comprises soaps or syndets.

19. Osteoinductive material according to claim 1, wherein the morphogenetic protein(s) is covalently or noncovalently linked to polyethylene glycols.

20. Osteoinductive material according to claim 1, wherein the buffer or solvent used for acidic coating contains HCl or sodium acetate.

21. Osteoinductive material according to claim 1, wherein the buffer or solvent used for basic coating contains NaOH or sodium carbonate/sodium bicarbonate.

22. Process for the production of an osteoinductive material according to claim 1, said process comprising contacting a matrix material with a solution of at least one morphogenetic protein characterized in that substances contained in said solution are selected to enable adjustment of the pH of the solution to below 5.2 even when in contact with the matrix material.

23. Process for the production of an osteoinductive material according to claim 1, said process comprising contacting a matrix material with a solution of a morphogenetic protein characterized in that substances contained in said solution are selected to enable adjustment of the pH of the solution to above 9.5 even when in contact with the matrix material.

24. A method of treating a patient in need of osteoinduction, comprising administering an effective amount of osteoinductive material of claim 1 to the patient.

25. In a method of treating a patient in need of osteoinduction by administering an effective amount of monomeric or dimeric morphogenetic proteins to the patient, the improvement comprising administering the osteoinductive material of claim 1 to the patient.

* * * * *